(12) United States Patent
Roussev et al.

(10) Patent No.: US 9,534,981 B2
(45) Date of Patent: Jan. 3, 2017

(54) PRISM-COUPLING SYSTEMS AND METHODS FOR CHARACTERIZING ION-EXCHANGED WAVEGUIDES WITH LARGE DEPTH-OF-LAYER

(71) Applicant: CORNING INCORPORATED, Corning, NY (US)

(72) Inventors: Rostislav Vatchev Roussev, Painted Post, NY (US); Vitor Marino Schneider, Painted Post, NY (US); Emily Elizabeth Young, Erin, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 14/966,642

(22) Filed: Dec. 11, 2015

(65) Prior Publication Data

US 2016/0178477 A1 Jun. 23, 2016

Related U.S. Application Data

(60) Provisional application No. 62/151,015, filed on Apr. 22, 2015, provisional application No. 62/095,945, filed on Dec. 23, 2014.

(51) Int. Cl.
*G01B 11/16* (2006.01)
*G01M 11/08* (2006.01)
(Continued)

(52) U.S. Cl.
CPC ............ *G01M 11/08* (2013.01); *C03C 21/002* (2013.01); *G01L 1/248* (2013.01); *G01N 21/41* (2013.01);
(Continued)

(58) Field of Classification Search
CPC ...................................................... G01B 11/62
(Continued)

(56) References Cited

U.S. PATENT DOCUMENTS 3,308,394 A 3/1967 Snitzer et al.
3,433,611 A 3/1969 Saunders et al.
(Continued)

FOREIGN PATENT DOCUMENTS

JP 5531944 3/1980
JP 57157130 9/1982
(Continued)

OTHER PUBLICATIONS

Invitation to Pay Additional Fees; PCT/US2015/066022; Mailed April 5, 2016.
(Continued)

*Primary Examiner* — Roy M Punnoose
(74) *Attorney, Agent, or Firm* — Timothy M. Schaeberle

(57) ABSTRACT

Prism-coupling systems and methods for characterizing large depth-of-layer waveguides formed in glass substrates are disclosed. One method includes making a first measurement after a first ion-exchange process that forms a deep region and then performing a second measurement after a second ion-exchange process that forms a shallow region. Light-blocking features are arranged relative to the prism to produce a mode spectrum where the contrast of the mode lines for the strongly coupled low-order modes is improved at the expense of loss of resolution for measuring characteristics of the shallow region. Standard techniques for determining the compressive stress, the depth of layer or the tensile strength of the shallow region are then employed. A second measurement can be made using a near-IR wavelength to measure characteristics of the deeper, first ion-
(Continued)

exchange process. Systems and methods of measuring ion-exchanged samples using shape control are also disclosed.

20 Claims, 13 Drawing Sheets

(51) Int. Cl.

| | |
|---|---|
| *G02B 6/134* | (2006.01) |
| *G02B 6/34* | (2006.01) |
| *G02B 6/14* | (2006.01) |
| *G02B 6/36* | (2006.01) |
| *G01L 1/24* | (2006.01) |
| *C03C 21/00* | (2006.01) |
| *G01N 21/41* | (2006.01) |
| *G01N 21/84* | (2006.01) |
| *G01B 11/22* | (2006.01) |
| *G01N 21/23* | (2006.01) |
| *G02B 5/04* | (2006.01) |
| *G01B 11/06* | (2006.01) |

(52) U.S. Cl.
CPC ......... *G01N 21/8422* (2013.01); *G02B 6/1345* (2013.01); *G02B 6/14* (2013.01); *G02B 6/34* (2013.01); *G02B 6/362* (2013.01); *G01B 11/0641* (2013.01); *G01B 11/22* (2013.01); *G01L 1/24* (2013.01); *G01N 21/23* (2013.01); *G01N 2021/4126* (2013.01); *G02B 5/04* (2013.01)

(58) Field of Classification Search
USPC .......................................................... 356/32
See application file for complete search history.

(56) References Cited

U.S. PATENT DOCUMENTS

| | | | |
|---|---|---|---|
| 3,873,209 A | 3/1975 | Schinke et al. | |
| 3,883,221 A | 5/1975 | Rigrod | |
| 4,207,000 A | 6/1980 | Miller | |
| 4,353,649 A | 10/1982 | Kishii | |
| 4,637,684 A | 1/1987 | Tomita et al. | |
| 4,655,589 A | 4/1987 | Cestaro et al. | |
| 5,164,589 A | 11/1992 | Sjodin | |
| 5,446,534 A | 8/1995 | Goldman | |
| 6,731,388 B1 | 5/2004 | Simon et al. | |
| 7,193,719 B2 | 3/2007 | Meehan et al. | |
| 8,957,374 B2* | 2/2015 | Liu ........................... | G01J 4/04 250/338.1 |
| 9,140,534 B2 | 9/2015 | Manlay | |
| 9,140,543 B1 | 9/2015 | Allan et al. | |
| 2010/0028607 A1 | 2/2010 | Lee et al. | |
| 2012/0106164 A1 | 5/2012 | Michaelis et al. | |
| 2014/0092377 A1* | 4/2014 | Liu ........................... | G01J 4/04 356/51 |
| 2014/0118740 A1 | 5/2014 | Fontaine et al. | |
| 2014/0368808 A1 | 12/2014 | Roussev | |
| 2015/0066393 A1 | 3/2015 | Liu et al. | |
| 2015/0116713 A1* | 4/2015 | Roussev ................. | G02B 6/34 356/365 |
| 2015/0338308 A1 | 11/2015 | Li et al. | |

FOREIGN PATENT DOCUMENTS

| | | |
|---|---|---|
| JP | 4310836 | 11/1992 |
| JP | 11281501 | 10/1999 |
| JP | 2002131224 | 5/2002 |

OTHER PUBLICATIONS

McRae et al; "The measurement of compression stress in egg-shells"; Journal of Agricultrual Engineering Research, vol. 14, No. 1, Mar. 1, 1969.
PCT/US2014/053069 Search Report Dated December 9, 2014.
Agan et al; "Stress effects in prism coupling measurements of thin polymer films"; App. Phys. A 80, 341-345 2005.
Brandenburg; "Stress in ion-exchanged glass waveguides"; Journal of Lightwave Technology, vol. LT4, No. 10, Oct. 1986.
Chiang et al; "Refractive-Index Profiling of buried planar waveguides by an inverse Wentzel-Kramer-Brillouin method"; Journal of Lightwave Technology, vol. 26, No. 11, Jun. 2008 pp. 1367-1373.
Chiang et al; "Refractive-Index Profiling of Graded-Index Planar Waveguides from Effective Indexes Measured with Different External Refractive Indexed"; Journal of Lightwave Technology, vol. 18, No. 10, Oct. 2000 pp. 1412-1417.
Kishii; "Surface Stress Meters Utilizing the Optical Waveguide Effect of Chemically Tempered Glasses"; Optics and Lasers in Engineering, 4 (1983) 25-38.
Metricon 2010 manual, Metricon corporation.
PCT/2014/062370 Search Report Dated Feb. 9, 2015.
Pelletier et al; "Optical characterization of thin films by guided waves"; Applied Optics; vol. 28, No. 14, Jul. 1989 pp. 2918-2924.
Pitt et al; "Lightguiding in langmuir-blodgett films"; Thin solid films, 68 (1980) 101-127.
Rau et al; "Prism coupled Terahertz waveguide sensor"; Applied Physics Letters, 86, 211119 (2005).
Surface Stress Meter FSM-60 Manual, Orihara Industrial Co.
Surface Stress Meter FSM-6000 Manual, Orihara Industrial Co.
Tien et al.; "Theory of Prism-Film Coupler and Thin-Film Light Guides"; Journal of the Optical Society of America, vol. 60, No. 10 (Oct. 1970); pp. 1325-1337.
Tien, "Light waves in thin films and integrated optics", Applied Optics 10, p. 2395 (1971).
Ulrich et al.; "Measurement of Thin Film Parameters with a Prism Coupler"; Applied Optics, vol. 12, No. 12 (Dec. 1973); pp. 2901-2908.
Ulrich; "Theroy of the prism-film coupler by plane-wave analysis"; Journal of the Optical Society of America; vol. 60, No. 10, 1970, pp. 1337-1350.
Zernike et al,; "Improved Version of the Evanescent-Wave Coupler", IEEE Journal of Quantum Electronics, Sep. 1970, pp. 577-578.
European Patent Office; International Search Report and Written Opinion for International Application No. PCT/US2015/066022; Mail Date: Jun. 24, 2016; pp. 1-21.

* cited by examiner ered
PRISM-COUPLING SYSTEMS AND METHODS FOR CHARACTERIZING ION-EXCHANGED WAVEGUIDES WITH LARGE DEPTH-OF-LAYER

CROSS-REFERENCE TO RELATED APPLICATIONS

This application claims priority under 35 USC §119(e) from U.S. Provisional Patent Application Ser. No. 62/095,945, filed on Dec. 23, 2014, and claims priority under 35 USC §119(e) from U.S. Provisional Patent Application Ser. No. 62/151,015, filed on Apr. 22, 2015 and which is incorporated by reference herein.

FIELD

The present disclosure relates to prism-coupling systems and methods for characterizing waveguides, and in particular relates to systems and methods for characterizing ion-exchange waveguides that have a large depth-of-layer.

The entire disclosure of any publication or patent document mentioned herein is incorporated by reference, including U.S. patent application Ser. No. 13/463,322, entitled "Systems and methods for measuring the stress profile of ion-exchanged glass," and in U.S. Patent Application Publication No 2014/0092377, entitled "Systems and methods for measuring birefringence in glass and glass-ceramics," U.S. Provisional Patent Application Ser. No. 61/897,546, entitled "Apparatus and methods for measurement of mode spectra of index profiles containing a steep region," (hereinafter, the '546 application), and U.S. Provisional Patent Application Ser. No. 62/001,116, entitled "Prism-coupling systems and methods for characterizing large depth-of-layer waveguides," filed on May 21, 2014.

BACKGROUND

Prism-coupling techniques can be used to measure the spectrum of guided modes of a planar optical waveguide to characterize the waveguide properties, e.g., to measure the refractive index and stress profiles. This technique has been used to measure the stress and the depth-of-layer (DOL) of different ion-exchanged (IOX) glasses used for a variety of applications, such as for cover glasses for displays (e.g., for smart phones).

Certain types of IOX glasses are actual dual IOX (DIOX) glasses formed by first and second diffusions that give rise to a two-segment profile. The first segment is adjacent the surface and has a relatively steep slope, while the second segment extends deeper into the substrate but has a relatively shallow slope. Such DIOX profiles are used for certain types of chemically strengthened glasses and anti-microbial glasses.

Such two-segment profiles result in a relatively large spacing between low-order modes, which have a relatively high effective index, and a very small spacing between high-order modes, which have a relatively low effective index. The spacing between modes is of interest since the modes are detected as lines in a mode spectrum by a photodetector (i.e., a digital camera). The resolution of the measurement is defined by the number of photodetector pixels between adjacent modes.

This distribution of the modes over the photodetector pixels is problematic when precise measurements of the deeper segment of the DIOX profile are sought because the high-order modes that travel in the deeper segment are under-sampled. If the DOL is large enough (e.g., greater than 70 μm or 100 μm or even greater than 140 μm or 150 μm,) it becomes impossible to adequately resolve the spectral lines of high-order modes, and as a result the DIOX profile cannot be precisely measured. In addition, for large DOL, the waveguide shape starts to become an issue and can adversely affect measurement quality.

One option for obtaining the required measurement resolution is to have a larger photodetector with more pixels, which in some cases may also require a larger-aperture optical system. However, such photodetectors and larger-aperture optical systems add substantial cost and complexity to the measurement system.

SUMMARY

Aspects of the disclosure relate to systems and methods for measuring characteristics of waveguides formed in a glass substrate by an IOX process (including a DIOX process) to control of fabrication process and product quality of chemically strengthened glasses. The refractive index profile (which corresponds to a stress profile) formed by the IOX process can have a deep region R2 with a DOL deeper than 100 μm, and a shallow region R1 having relatively high slope of the refractive index as a function of depth.

Currently, high-throughput measurements of chemically strengthened glass for fabrication and quality control are performed using the conventional prism-coupling systems that have high precision and speed but DOL-measurement limitations, especially beyond 100 μm. Conventional prism-coupling measurement systems also assume a linear refractive index profile, which is a poor approximation for many IOX-formed profiles (including DIOX-formed profiles) that have a large DOL.

The systems and methods disclosed herein provide for effective control of production, product quality, and frangibility of DIOX waveguides by using a prism-coupling system optimized separately for the shallow and steep region adjacent the surface and for the deep and gradual DOL region below the shallow and steep region.

In one embodiment, a prism-coupling system is optimized for high resolution and used to measure the compressive stress (CS) and DOL after a first IOX fabrication step that produces a very deep compression region R2 having a DOL above about 70 μm or more, and preferably 100 μm or more. These measurements are denoted CS1 and DOL1 and are verified to conform to requirements of the fabrication process. The tensile strength (CT) is also verified to conform to a CT requirement, which is consistent with a CT budget allowed for fabrication step 1. A second IOX fabrication step ("step 2") produces a steep near-surface region R1 having a depth typically on the order of 10-15 micrometers, and high CS, typically >500 MPa, and most often >700 MPa.

In a second aspect of the disclosure, a prism-coupling system is configured to include light-blocking features arranged to produce a mode spectrum where the contrast of the mode lines for the strongly coupled low-order modes is improved at the expense of loss of resolution in the higher-order modes. The collected optical signal is produced from an illuminated region whose length is preferably about 8 mm or smaller.

In a preferred embodiment, the system is configured to have reduced resolution using light-blocking features such that the dense spectrum of (higher-order) modes propagating in the deep region is not resolved, while the sparse (lower-order) modes confined to the shallow, steep region R2 are well resolved. Then standard measurements for CS, DOL and CT can be used to measure the CS and DOL of the shallow region, as well as an effective CT that is required to conform to a budgeted CT for the shallow region R1 formed in fabrication step 2.

With separate measurement control for IOX processes of fabrication steps 1 and 2, the regions R1 and R2 of the refractive index profile extending from the surface (at the time of measurement) are well-approximated as a simple linear truncated index profile. This allows for conventional calculations to be used to correctly to determine the required CS and DOL for each region R1 and R2 of the profile, as well as the budgeted CT for each region of the profile, thereby allowing full control of profile conformance to fabrication requirements, as well as frangibility conformance.

In an example, the prism-coupling system is configured to allow ultra-high resolution measurements by having a relatively large prism (preferably longer than 15 mm, and as a good example, 25 mm long), and a combination of optics and a photodetector (e.g., camera sensor) that allow for resolving mode lines that are separated by $10^{-4}$ refractive index units (RIU) or less, ideally resolving mode lines separated by as little as $5 \times 10^{-5}$ RIU.

With a prism having a base angle of 60° and refractive index about 1.72, and a refractive index of about 1.49, such combination of optics and photodetector may include a lens with focal length of f=200 mm and relatively low aberrations, with the photodetector being in the form of a camera sensor having pixels smaller than about 5 μm, with preferably more than 800 columns of such pixels over which each of the TE and TM mode spectra is captured.

The systems and methods disclosed herein have a number of advantages. One advantage is the independent optimization of the measurement of deep and shallow regions, which allows for greater control of deeper refractive-index profiles, when a near-surface shallow region of high CS is a requirement for the profile. Another advantage is that existing robust software for linear profiles can be used to swiftly and effectively measure and control the product quality for DIOX profiles having very large DOL. In addition, CT budgeting for IOX fabrication steps 1 and 2 can be effectively enforced, thereby avoiding frangibility while operating relatively close to the frangibility limit for maximum chemical strengthening.

Other aspects of the disclosure include systems and methods for effective control of production, product quality, and frangibility of DIOX glass, by using prism-coupling instruments optimized separately for large-DOL measurement, and for an optional shallow, steep-region measurement using a light source that emits near-IR light.

In one aspect of the disclosure, the prism-coupling system is optimized by using a near-IR light source for high resolution and to capture the CS/DOL after the first IOX fabrication step that produces a very deep compression region R2 having a DOL above about 70 μm or greater, and especially above 100 μm. The CS1 and DOL1 values are verified to conform to requirements of the fabrication process. The CT value of IOX fabrication step 1 is also verified to conform to a CT1 requirement, which is consistent with a CT budget.

The second IOX fabrication step produces a steep near-surface region R1 having a depth typically in the range from about 10 to about 15 μm, and a high CS, typically >500 MPa, and most often >700 MPa. In a second aspect of the disclosure, the prism-coupling instrument employs a near-IR light source and light-blocking features arranged to produce and measure a mode spectrum where the contrast of the mode lines for the strongly coupled low-order modes is improved at the expense of resolution of the higher-order modes.

In an example, the collected optical signal is produced from an illuminated region whose length is preferably about 8 mm or smaller. In one embodiment, the prism-coupling system is configured to have reduced resolution by using the aforementioned light-blocking features so that the dense spectrum of modes propagating in the deep region R2 are not resolved, while the sparse modes confined to the shallow steep region are resolved. Then standard techniques for determining CS, DOL and CT of the shallow region R1 are used, as well as an effective CT contribution that is required to conform to a budgeted CT.

In another embodiment, the deep region R2 of the profile of a DIOX substrate is measured using a prism-coupling system configured to operate at a near IR wavelength, while the shallow steep portion is measured using a shorter, visible wavelength. In a related embodiment, the two measurements are enabled in a single prism-coupling system having an IR light source and a visible light source, where the two sources can be switched between measurements. In an example, the prism-coupling system employs light-blocking features used for measuring the shallow and steep region R1 at the visible wavelength.

The number of mode lines in the mode spectrum of a near-IR imaging prism-coupling system is smaller than for a similar system operating at λ=589 nm. This corresponds to an increase in the mode-line spacing, which makes the measurements less sensitive to small amounts of warp in the samples, which can be a major driver of the increased standard deviations in measurements of stress with large DOL>100 μm. In addition, the increase in mode-line spacing helps improve the sampling of the mode lines by the camera sensor, which further helps resolve the mode lines and reduce DOL errors, particularly for DOL>150 μm.

Other aspects of the disclosure are directed to systems and method for improving the speed of prism-coupling-based measurements of large DOL waveguides, and eliminating the need to slide and spin the measured sample for finding an optimum measurement condition. The systems and methods rely on imparting a similar warp or shape, preferably a similar minimized warp or shape, on each measured sample. This is accomplished by using a chuck assembly that has a rigid platen configured to either define the sample shape to be that of the chuck, or to apply an air cushion to force the sample to adopt the flat coupling surface shape of the prism. The imparted repeatable shape is the same or very close to the nominal design shape of the measured glass in the area of measurement, to limit to only a few MPa or less the changes of surface stress in the measured glass resulting from the shape control. More specifically, the error in surface stress introduced by the shape control method must be acceptable within the context of the use of the measurement for quality control.

In one example, the shape-controlling platen of the chuck assembly is made of a porous material or that has small through channels, with the chuck being operably connected to a vacuum source (e.g., a vacuum pump). The chuck assembly applies the vacuum to the sample through its pores or through channels, such that the sample is sucked onto the platen, thereby making the sample substantially conform to the surface shape of the platen. This makes all the samples being measured have the shape of the platen over an area of adequate size for high-resolution prism coupling measurements. If the platen uses through channels to apply suction to the sample, in an example the channels are spaced less than about 1 cm apart, and in another example are spaced less than about 5 mm apart. In addition, it is preferable that the diameter of each of the channels is less than about 2 mm, and more preferable is less than about 1 mm.

The above chuck-based embodiment works well when the sample thickness is very uniform. If the sample thickness varies significantly over the measurement area, and this variation is substantially different from one sample to the next, then adopting the shape of the platen on the back surface of the sample does not guarantee that the measurement sample surface facing the prism will have the same shape every time. Thus, in another embodiment, a function of the chuck assembly is to provide an air cushion (e.g., air having pressure somewhat higher than the ambient pressure) on the back side of the sample, so that the sample is pressed uniformly against the prism. This tends to force the sample coupling surface to conform to the shape of the prism coupling surface. This embodiment works also for samples with moderate thickness variation across the measurement area. This is because it is the measurement surface of the sample facing the prism that is under requirement to conform to a pre-defined surface (in this case, the prism contact surface).

In another embodiment, suction is applied to the sample through channels in the prism itself, forcing the sample coupling surface to substantially conform to the prism coupling surface. In one example, coupling between the prism and the substrate is mediated by refractive-index liquid having an index approximately equal to the prism index. In another example, coupling is mediated by a liquid having refractive index higher than the substrate surface index by at least 0.08. In another example, coupling is mediated by a liquid having refractive index lower than that of the substrate. In a specific version of this embodiment, the prism coupling surface may be coated with a thin dielectric layer having an index preferably lower than the oil index. In another example, optical coupling is mediated by air or another gas diluted by the effect of suction applied through the prism by a vacuum system.

In another embodiment, the application of a vacuum through channels in the prism is combined with pressure applied via the chuck assembly on the back side of the sample.

Advantages of the shape-control measurement methods include reduced measurement time, reduced risk of damage from moving the sample, increased DOL precision, control of gravity-induced shape variations that occur with large samples, and the ability to handle shape variations in a sample.

Additional features and advantages are set forth in the Detailed Description that follows, and in part will be readily apparent to those skilled in the art from the description or recognized by practicing the embodiments as described in the written description and claims hereof, as well as the appended drawings. It is to be understood that both the foregoing general description and the following Detailed Description are merely exemplary and are intended to provide an overview or framework to understand the nature and character of the claims.

BRIEF DESCRIPTION OF THE DRAWINGS

The accompanying drawings are included to provide a further understanding and are incorporated in and constitute a part of this specification. The drawings illustrate one or more embodiment(s) and together with the Detailed Description serve to explain principles and operation of the various embodiments. As such, the disclosure will become more fully understood from the following Detailed Description, taken in conjunction with the accompanying Figures, in which.

DETAILED DESCRIPTION

Reference is now made in detail to various embodiments of the disclosure, examples of which are illustrated in the accompanying drawings. Whenever possible, the same or like reference numbers and symbols are used throughout the drawings to refer to the same or like parts. The drawings are not necessarily to scale, and one skilled in the art will recognize where the drawings have been simplified to illustrate the key aspects of the disclosure.

The claims as set forth below are incorporated into and constitute part of this Detailed Description.

Cartesian coordinates are shown in some of the Figures for the sake of reference and are not intended to be limiting as to direction or orientation.

The abbreviation RIU stands for "refractive index units."

The discussion below refers to lower-order modes and higher-order modes of the waveguide formed by an IOX process, which in examples can be a single IOX process or a double IOX process (DIOX). The modes are ordered by the number of zeroes (nodes) in the depth distribution of the electric field amplitude. The lowest-order mode (labeled $TM_0$ for transverse-magnetic modes and $TE_0$ for transverse-electric modes) has no zeroes in the distribution, and has the highest effective index. The second mode ($TM_1$ or $TE_1$), has one node in the depth distribution of its electric field amplitude, and the second-highest effective index, and so on. The highest-order guided mode for each of the two polarization states supported by the waveguide has the most zeroes in the depth distribution of electric field amplitude, and the lowest effective index among the modes of that polarization state.

In many examples pertaining to chemically strengthened glasses with large DOL, a strengthening ion (such as $K^+$ in the ion exchange $K^+$ for $Na^+$) is used and the effective index of the highest-order mode may be only slightly higher than the substrate or bulk glass index, and the effective index of the lowest-order (fundamental) mode may be only slightly lower than the maximum value of the material refractive index anywhere inside the waveguide (often occurring at the glass surface).

Thus, the terms "higher-order mode" and "lower-order mode" as used herein are somewhat relative in that we may define for the sake of convenience a certain number of the lowest-order modes to collectively be "low-order modes" and the remaining modes that are higher to constitute "higher-order modes." Consequently, the particular distinction used to differentiate between the modes or to refer to the modes as being in different groups is for ease of description and is not intended to be limiting.

In the discussion below, the substrate 20 is also referred to below as "sample 20" or just "sample."

IOX and DIOX Substrates

Figure 1A:
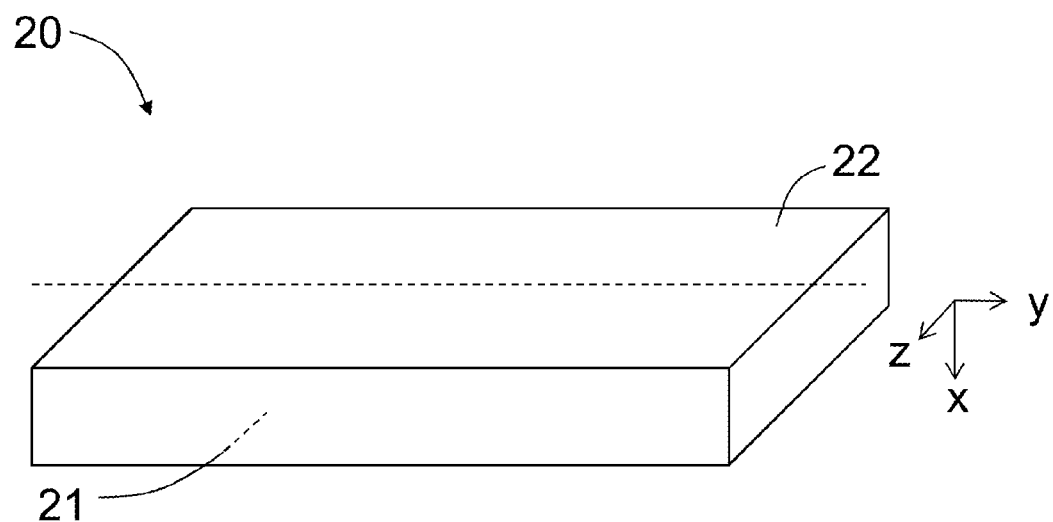
FIG. 1A is an elevated view of an example DIOX glass substrate in the form of a planar substrate.
Figure 1B:
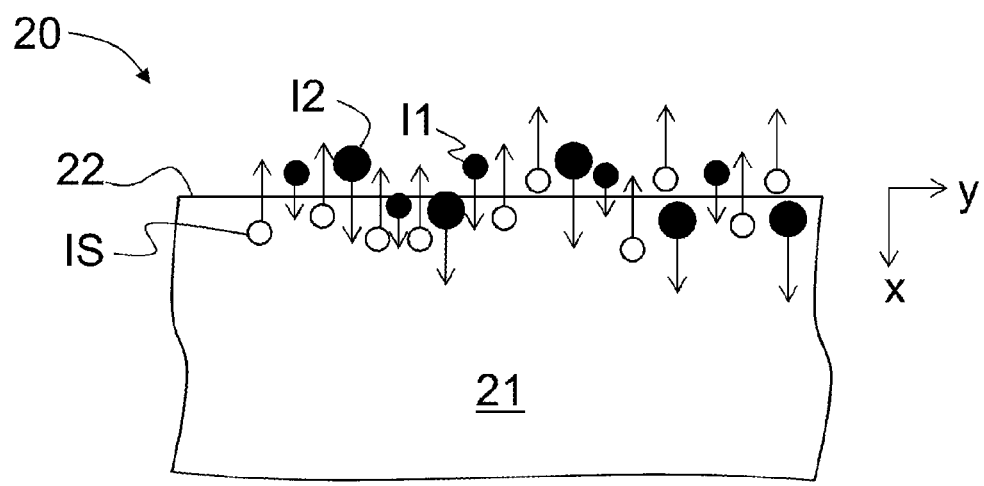
FIG. 1B is a close-up cross-sectional view of the DIOX substrate of FIG. 1A as taken in the x-y plane and that illustrates the double ion-exchange process that takes place across the substrate surface and into the body of the substrate.

FIG. 1A is an elevated view an example glass substrate in the form of a planar ion-exchanged substrate 20 that has a body 21 and a (top) surface 22, wherein the body has a base (bulk) refractive index $n_s$ and a surface refractive index $n_0$. FIG. 1B is a close-up cross-sectional view of ion-exchanged substrate 20 as taken in the x-y plane and illustrates an example double ion-exchange (DIOX) process that takes place across surface 22 and into body 21 in the x-direction.

Figure 1C:
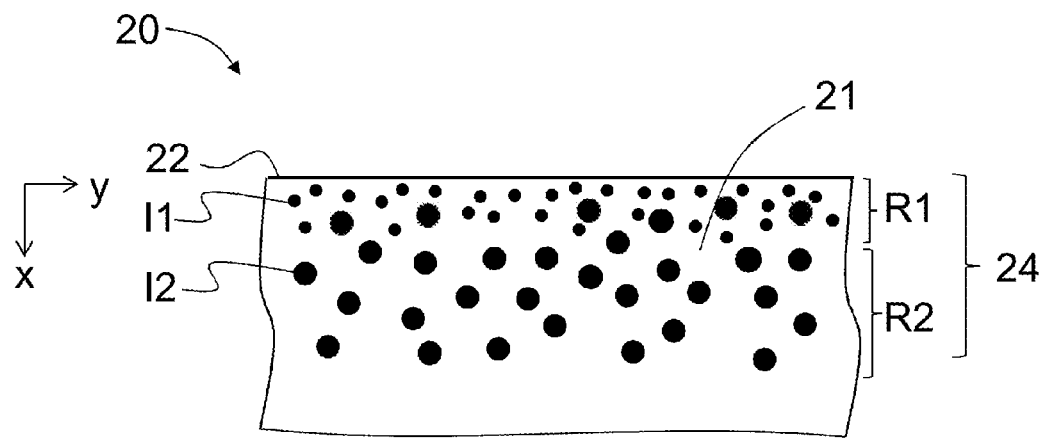
FIG. 1C schematically illustrates the result of the DIOX process that forms the DIOX substrate.

FIG. 1C schematically illustrates the result of a DIOX process on substrate 20. The substrate 20 includes substrate ions IS in body 21 that exchange for first ions I1 and second ions I2. The first and second ions I1 and I2 can be introduced into the glass body either sequentially or concurrently using known techniques. For example, second ions I2 can be $K^+$ ions introduced via a $KNO_3$ bath for strengthening, prior to introducing first ions I1 that can be $Ag^+$ ions introduced via a $AgNO_3$-containing bath to add the anti-microbial property adjacent surface 22. The circles in FIG. 1B that represent ions I1 and I2 are used for schematic illustration only, and their relative sizes do not necessarily represent any actual relationship between the sizes of the actual ions participating in the ion exchange.

In addition, ions I1 may be present in significant numbers in both regions R1 and R2 (see FIG. 2, introduced and discussed below) as may be ions of type I2. Even with a one-step IOX process, it is possible to observe the formation of two regions R1 and R2, with significant differences in the relative concentrations of ions I1 and I2. In an example, using an ion exchange of Na-containing glass in a bath containing a mixture of $KNO_3$ and $AgNO_3$, it is possible to obtain region R1 with significant concentrations of both $Ag^+$ and $K^+$, and region R2 also with significant concentrations of $Ag^+$ and $K^+$, but the relative concentration of $Ag^+$ with respect to $K^+$ may be significantly larger in region R1 than in region R2. Regions R1 and R2 define a waveguide region ("waveguide") 24 adjacent surface 22 of substrate 20.

Figure 2:
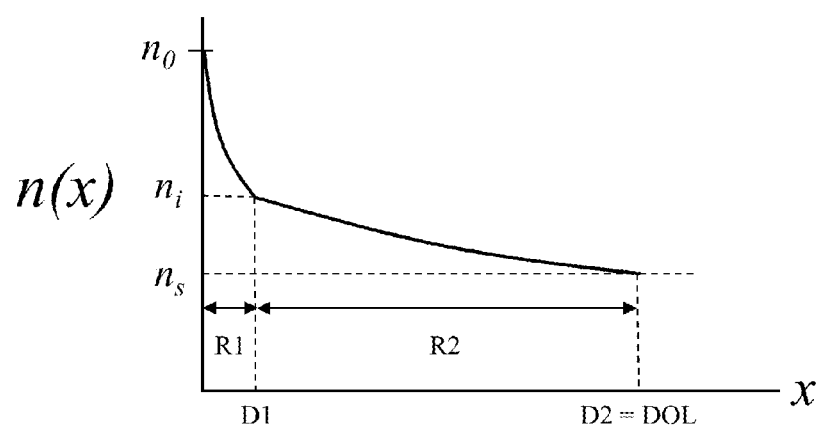
FIG. 2 is a representation of an example refractive index profile n(x) for the DIOX substrate illustrated in FIG. 1C.

FIG. 2 is a representation of an example refractive index profile n(x) for substrate 20 such as illustrated in FIG. 1C that has undergone a DIOX process. The refractive index profile n(x) includes a first region R1 associated with the shallower ion-exchange (ions I1) and that has a depth D1 into body 21. The refractive index profile n(x) also includes a second region R2 associated with the deeper ion-exchange (ions I2) and that has a depth D2 that defines the depth-of-layer (DOL). In an example, DOL is at least 50 μm and further in an example can be as large as 150 μm. In another example DOL is 70 μm or greater, or 100 μm or greater.

The deeper second region R2 may be produced in practice prior to the shallower region. The region R1 is adjacent substrate surface 22 and is relatively steep and shallow (e.g., D1 is a few microns), whereas region R2 is less steep and extends relatively deep into the substrate to the aforementioned depth D2. In an example, region R1 has a maximum refractive index $n_0$ at substrate surface 22 and steeply tapers off to an intermediate index $n_i$, while region R2 tapers more gradually from the intermediate index down to the substrate (bulk) refractive index $n_s$. It is emphasized here that other ion-exchanged processes can result in a steep and shallow near-surface refractive index change and that a double ion-exchange process is discussed here by way of illustration. The portion of the refractive index profile n(x) for region R1 represents a "spike" in the refractive index.

In an example, the methods disclosed herein employ optical measurements of substrate 20 as formed using an IOX or DIOX process. The measurements are performed using a prism-coupling system as described below. Such systems that employ a conventional coupling prism are generally known in the art, and example systems suitable for use in carrying out the methods of the present disclosure with the modifications set forth below are described in the above-identified U.S. patent applications.

Prism-Coupling System

Figure 3A:
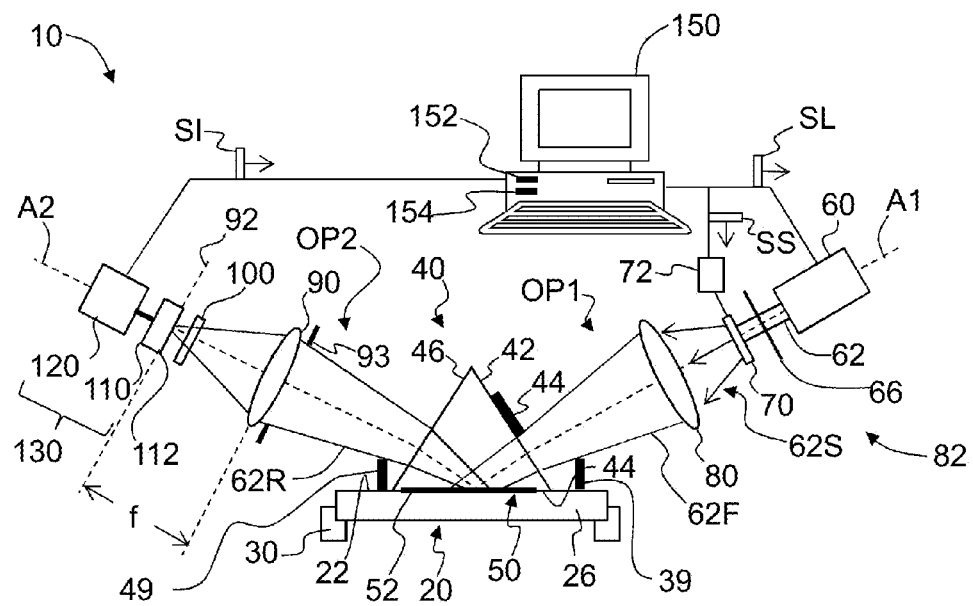
FIG. 3A is a schematic diagram of an example prism-coupling system according to the disclosure.
Figure 3B:
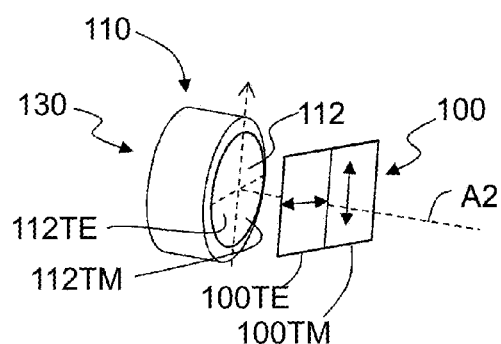
FIG. 3B is a close-up view of the photodetector system of the prism-coupling system of FIG. 3A.

FIG. 3A is a schematic diagram of an example prism-coupling system 10 suitable for carrying out the methods of measuring the TE and TM mode spectra for substrate 20 having a refractive profile n(x) such as shown in FIG. 2. FIG. 3B is a close-up view of the photodetector system of prism-coupling system 10 of FIG. 3A. In an example, substrate 20 constitutes a chemically strengthened glass such as GORILLA® glass, made by Corning, Inc., of Corning, N.Y.

The prism-coupling system 10 includes a substrate holder 30 configured to hold substrate 20. In alternative embodiments, however, substrate holder 30 is not required. The prism-coupling system 10 also includes a coupling prism 40 that has an input surface 42, an optional top flat surface 41

Figure 20A:
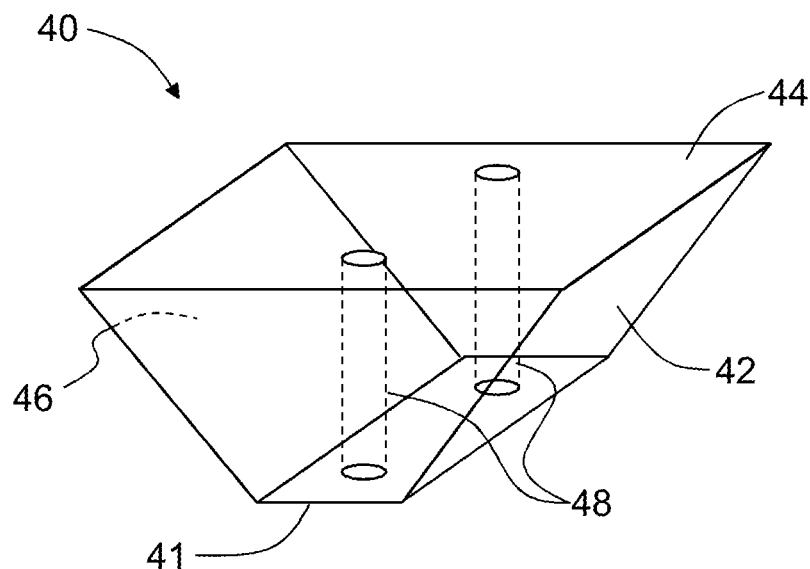
FIGS. 20A and 20B are elevated views of an example prism that includes channels that can be used to establish a vacuum at the coupling surface of the prism to cause the substrate to substantially conform to the shape of the coupling surface.
Figure 20B:
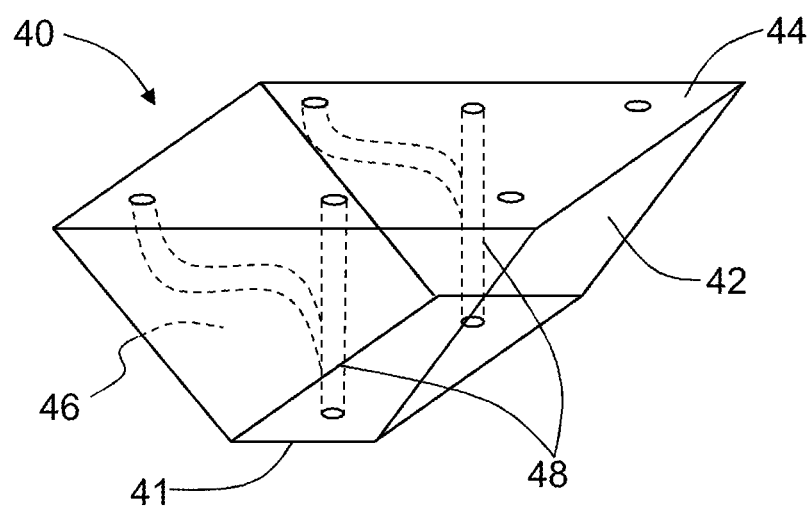

(see, e.g., FIG. 20A), a coupling surface 44 and an output surface 46. The coupling prism 40 has a refractive index $n_p > n_0$. The coupling prism 40 is interfaced with the top surface ("coupling surface") 22 of substrate 20 by bringing coupling-prism coupling surface 44 and substrate top surface into optical contact, thereby defining a substrate-prism interface ("interface") 50 that optionally includes an interfacing fluid (not shown).

The coupling prism 40 includes an output-side prism angle ("prism angle") α that measures the angle formed by output surface 46 and coupling surface 44. An example prism angle α is 60°, but other angles can be used effectively.

With continuing reference to FIG. 3A, prism-coupling system 10 includes optical axes A1 and A2 that respectively pass through input and output surfaces 42 and 46 of coupling prism 40 to generally converge at interface 50 after accounting for refraction at the prism/air interfaces. The prism-coupling system 10 includes, in order along axis A1, a light source 60 that emits measuring light 62 of wavelength λ, an optional optical filter 66 that may be alternatively included in the detector path on axis A2, an optional light-scattering element 70 that forms scattered or diffuse light ("diffuse light") 62S, and an optional focusing optical system 80 that may partially focus light 62 or 62S, as explained below. Thus, in an example of prism-coupling system 10, there are no optical elements between light source 60 and prism input surface 42. Light source 60, optional optical filter 66, optional light-scattering element 70 and optional focusing optical system 80 constitute a light source system 82. In the discussion below, it is assumed by way of example that scattered light 62S is coupled into waveguide 24 of substrate 20.

The system 10 also includes, in order along axis A2 from coupling prism 40, a collection optical system 90 having a focal plane 92 and a focal length f and that receives reflected light 62R as explained below, a polarizer system 100, and a photodetector system 130. An optional iris 93 can also be included adjacent collection optical system 90.

The axis A1 defines the center of an optical path OP1 between light source 60 and coupling-prism coupling surface 44. The axis A2 defines the center of an optical path OP2 between coupling surface 44 and photodetector system 130. Note that axes A1 and A2 may be bent at input and output surfaces 42 and 46, respectively, due to refraction. They may also be broken into sub-paths by the insertion of mirrors in optical paths OP1 and/or OP2.

In an example, photodetector system 130 includes a detector (camera) 110 and a frame grabber 120. In other embodiments discussed below, photodetector system 130 includes a CMOS or CCD camera. FIG. 3B is a close-up elevated view of polarizer system 100 and detector 110 of photodetector system 130. In an example, polarizer system 100 includes a TE polarizer section 100TE and a TM polarizer section 100TM. The photodetector system 130 includes a photosensitive surface or sensor 112. The photosensitive surface 112 resides in focal plane 92 of collection optical system 90, with the photosensitive surface being generally perpendicular to axis A2. This serves to convert the angular distribution of reflected light 62R exiting the coupling prism output surface 46 to a transverse spatial distribution of light at the sensor plane of camera 110. With reference to the close-up inset of FIG. 3B, in an example embodiment, photosensitive surface 112 comprises pixels 112p, i.e., detector 110 is a digital detector, such as a digital camera, and photosensitive surface 112 is a sensor such as a CMOS sensor.

Splitting photosensitive surface 112 into TE and TM sections 112TE and 112TM allows for the simultaneous recording of digital images of the angular reflection spectra (mode spectra) for the TE and TM polarizations of reflected light 62R. This simultaneous detection eliminates a source of measurement noise that could arise from making the TE and TM measurements at different times.

In another embodiment of system 10, polarizer system 100 does not have a split polarizer configuration but instead comprises a single polarizer, rotated sequentially 90 degrees between two states that transmit the TM or the TE spectrum, to sequentially take the TM and TE coupling spectra. In this embodiment, polarizer system 100 can be placed in either light source path OP1 or detector path OP2.

Figure 3C:
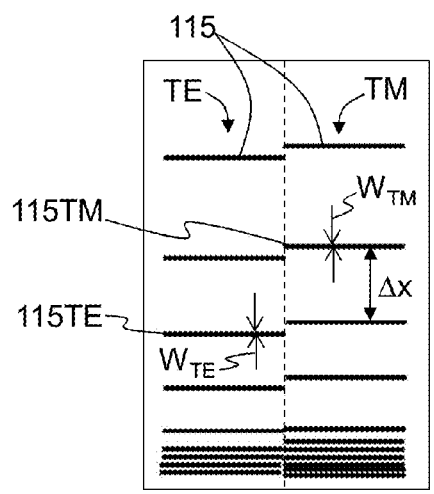
FIG. 3C is a schematic representation of TM and TE mode spectra as captured by the photodetector system of FIG. 3B.

FIG. 3C is a schematic representation of TM and TE mode spectra 113 associated with waveguide 24 and as captured by photodetector system 130. The mode spectra 113 includes mode lines 115. More specifically, the TM and TE mode spectra 113 are made up of respective spectral lines (mode lines) 115TM and 115TE having respective widths $W_{TM}$ and $W_{TE}$. The TM and TE mode spectra each include lower-order modes (i.e., high-effective-index modes) L-TE and L-TM and higher-order modes (i.e., low-effective-index modes) H-TE and H-TM. The spacing between adjacent mode lines 115 is denoted Δx and varies along the length of the given mode spectrum 113, getting increasingly smaller from the lower-order modes to the higher-order modes.

Example light sources 60 include lasers, light-emitting diodes, and broader-bandwidth sources such as hot-filament lamps and quartz lamps. In one example, light source system 82 is configured as a diffuse light source. Example operating wavelengths λ of measuring light 62 generated by light source 60 can include near-ultra-violet, visible and IR wavelengths. When light source 60 is coherent, the use of the aforementioned light-scattering element 70, which may be a moving or vibrating diffuser, can help mitigate speckle, which can be problematic for precise measurements of the mode lines 115.

The prism-coupling system 10 also includes a controller 150, which is configured to control the operation of the system. The controller 150 is also configured to receive and process image signals SI from photodetector system 130 that are representative of captured TE and TM mode spectra images. The controller 150 includes a processor 152 and a memory unit ("memory") 154. The controller 150 may control the activation and operation of light source 60 via a light-source control signal SL, and receives and processes image signals SI from photodetector system 130 (e.g., from frame grabber 120, as shown).

In an example, controller 150 comprises a computer and includes a reading device, for example, a floppy disk drive, a CD-ROM drive, a DVD drive, a magnetic optical disk (MOD) device (not shown) or any other digital device including a network-connecting device, such as an Ethernet device (not shown), for reading instructions and/or data from a non-transient computer-readable medium, such as a floppy disk, a CD-ROM, a DVD, a MOD, a flash drive or another digital source such as a network or the Internet. The controller 150 is configured to execute instructions stored in firmware and/or software (not shown), including signal-processing instructions for carrying out the measurements disclosed herein. In examples, the terms "controller" and "computer" are interchangeable.

The controller 150 is programmable to perform the functions described herein, including the operation of system 10 and the post-processing (signal processing) of image signals SI to arrive at a measurement of a characteristic of substrate 20, such as the stress profile S(x), birefringence, or compressive stress CS, or the refractive index profile n(x), which may include TE and TM components. As used herein, the term "computer" is not limited to just those integrated circuits referred to in the art as computers but broadly refers to computers, processors, microcontrollers, microcomputers, programmable logic controllers, application-specific integrated circuits and other programmable circuits, and these terms are used interchangeably herein.

Software may implement or aid in the performance of the operations of system 10 disclosed herein, including the aforementioned signal processing. The software may be operably installed in controller 150 and in particular in processor 152 and memory 154. Software functionalities may involve programming, including executable code, and such functionalities may be used to implement the methods disclosed herein. Such software code is executable by the general-purpose computer or by the processor unit described below.

In operation, the code and possibly the associated data records are stored within a general-purpose computer platform, within processor 152 and/or in memory 154. At other times, however, the software may be stored at other locations and/or transported for loading into the appropriate general-purpose computer systems. Hence, the embodiments discussed herein involve one or more software products in the form of one or more modules of code carried out by at least one non-transient machine-readable medium. Execution of such code by processor 152 of computer system 150 or by the processor unit enables the platform to implement the catalog and/or software downloading functions in essentially the manner performed in the embodiments discussed and illustrated herein.

The controller 150 and/or processor 152 may each employ a non-transient computer-readable medium or machine-readable medium (e.g., memory 154), which refers to any medium that participates in providing instructions to the processor for execution, including, for example, determining an amount of surface birefringence/stress or the stress profile S(x) of substrate 20. The memory 154 constitutes a non-transient computer-readable medium. Such a medium may take many forms, including but not limited to non-volatile media, volatile media and transmission media. Non-volatile media include, for example, optical or magnetic disks, such as any of the storage devices in any computer(s) operating as one of the server platforms discussed above. Volatile media include dynamic memory, such as the main memory of such a computer platform. Physical transmission media include coaxial cables, copper wire and fiber optics, including the wires that comprise a bus within a computer system.

Common forms of non-transient computer-readable media therefore include, for example, a floppy disk, a flexible disk, a hard disk, magnetic tape, flash drives and any other magnetic medium; a CD-ROM, a DVD and any other optical medium; less commonly used media such as punch cards, paper tape and any other physical medium with patterns of holes; a RAM, a PROM, an EPROM, a FLASH-EPROM and any other memory chip or cartridge; a carrier wave transporting data or instructions, cables or links transporting such a carrier wave, or any other medium from which a computer can read programming code and/or data. Many of these forms of computer-readable media may be involved in carrying one or more sequences of one or more instructions to processor 152 for execution.

In an example, controller 150 is programmed to determine at least one characteristic of ion-exchanged substrate 10 based on the measured mode spectra. Example characteristics include: surface stress, stress profile, compressive stress, depth-of-layer, refractive index profile and birefringence. In an example, controller 150 is programmed to carry out calculations as disclosed in the article by A. Brandenburg, "Stress in Ion-Exchanged Glass Waveguides," *Journal of Lightwave Technology* 4, no. 10 (October 1986): 1580-93, and as also disclosed in the aforementioned '546 application The prism-coupling system 10 may be a modified version of a commercial prism-coupling system, such as the FSM-6000 prism-coupling system made and sold by Orihara Industrial Co., Ltd., of Tokyo, Japan. This system is referred to below as the "FSM system." The FSM system uses the "m-line" method and represents the state of the art in high-throughput non-destructive measurements of stress in flat ion-exchanged glasses, and utilizes a coupling prism 40 with a prism index $n_p$=1.72 at 589 nm. The FSM system uses an index-matching fluid having an index $n_f$=1.64. In the FSM system, the surface compressive stress (CS) is calculated from the effective indices $n_{eff}$ of the first two TM and the first two TE modes, while the total number of observed modes is used along with the substrate index and the aforementioned effective indices of the first two modes for the DOL calculation based on a linear refractive-index profile assumption.

Two-Step Measurement Systems and Methods

In an example embodiment, the light source system 82 of FIG. 3A is configured to produce diffuse light 62S that illuminates the coupling surface 44 of the prism 40 over a relatively wide range or cone of input angles. The prism 40 couples this cone of diffuse light 62S into several possible different angles of incidence onto the substrate-prism interface 50. In an example, the aforementioned fluid such as an oil of certain refractive index is included in the substrate-prism interface 50. Typically the index of such a fluid is different from the index of the glass substrate to avoid difficulties and inaccuracies in the measurements. The diffuse light 62S for those incident angles that are phase-matched to the possible allowed light paths (modes) of the waveguide 24 formed in the surface 22 of sample 20 are coupled into the glass waveguide. The diffuse light (hereinafter, "light") 62S that is incident at other angles is not coupled into the waveguide 24.

The light 62R that is outputted from prism 40 at output surface 46 is imaged with the help of collection optical system 90 and a pattern of mode lines 115 is formed at the focal plane 92 where detector 110 resides (see FIG. 3C). Here, the black mode lines 115 correspond to the angles or equivalent refractive indices where the light 62S coupled into the waveguide 24 so that the light at these angles is not present in the mode spectrum 113. All other angles where the light 62S is not coupled are thus brighter. The position of the mode lines 115 can be described in terms of refractive index. If a polarizer system 100 is used in half of the output frame such as shown in FIG. 3A and FIG. 3B, one can then measure different polarizations (TM vs TE), as shown in FIG. 3C. If stress is present in the sample, the TE and TM mode lines 115TE and 115TM will not align with each other such as shown in FIG. 3C, indicating some stress-induced birefringence on the sample.

In an example method of measuring compressive stress CS at the surface 22 of substrate 20, the first 2 TM modes and the first 2 TE modes are used, along with some approximations to extrapolate the value of stress at the surface. To compute the DOL, one needs to have all the number of modes and the index difference between the surface and the deep interior of the substrate. By counting the number of mode lines 115 present in the TE and TM mode spectra, one can compute the approximated DOL for each polarization.

Figure 4:
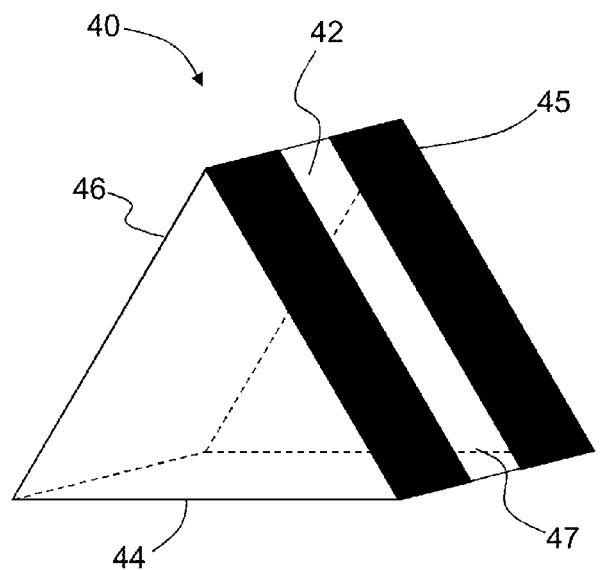
FIG. 4 is an elevated view of an example prism showing an example mask on the input face of the prism, wherein the mask defines a slit aperture.

In an example of prism-coupling system 10, the coupling prism 40 can be relatively large (e.g., 25 mm×25 mm at coupling surface 44). FIG. 4 is an elevated view of an example prism 40 that includes a mask 45 on the prism input face 42. The mask 45 defines a slit opening 47 that in an example has a width of between 1 mm and 20 mm. Another mask 45 can be used at the output face 46 of the prism 40 to define a corresponding slit 47 thereon to further restrict the range of spatial angles for light 62R. This masking technique can be used to improve detection and contrast of the numerous higher-order modes.

Figure 5:
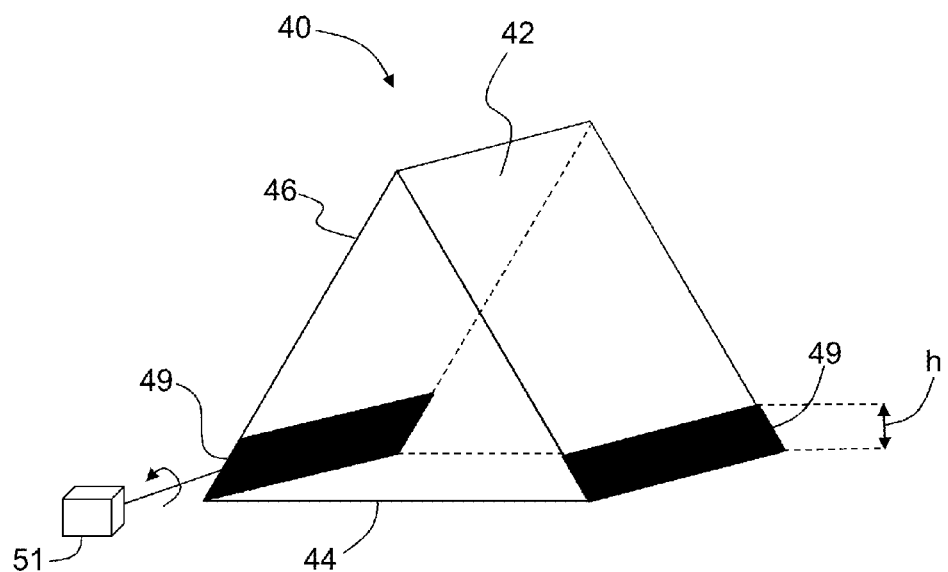
FIG. 5 is an elevated view of an example prism showing an example of light-blocking features on the input and output faces of the prism.

FIG. 5 is similar to FIG. 4 and illustrates an example wherein prism 40 includes at least one light-blocking feature 49 in the vicinity of the prism adjacent one or both of the input and output surfaces 42 and 46. Two example light-blocking features 49 are shown in FIG. 5. In this embodiment, the light-blocking features 49 can be used in combination with one or more masks 45. In an example, the light-blocking features 49 can be spaced apart from the prism 40 and can be vertical rather than angled (see FIG. 3A).

For the particular case of detecting the fundamental or low-order modes in the spike DIOX region R1 of waveguide 24, the light-blocking features 49 act to reduce the mode coupling and angular distribution of the fundamental and lower order modes, which are more separated at the photodetector 110, making them more easily visible. However, it also decreases the contrast of the high-order modes that are more numerous and more closely spaced at the photodetector 110. There is thus a trade-off of the imaging of the lower-order modes and higher-order modes in the case of a spike DIOX index profile, and the size (i.e., height h) of the light-blocking feature(s) 49 is chosen accordingly.

In an example, the height h of the light-blocking feature is in the range from 0.2 mm to 20 mm, with 2 mm being an exemplary height. The position of the light-blocking features 49 relative to the prism 40 can also vary. In various examples, the light-blocking features 49 reside at distances between 0 mm to 50 mm away from the corresponding prism surface. The light-blocking features 49 adjacent the input surface 42 serve to control the angle of incidence of input light 62S allowed to pass through the prism to interface 50.

As noted above, conventional prism-coupling systems like the FSM system work relatively well for single ion-exchange (SIOX) waveguide that have DOL<75 μm. For deeper values of single ion-exchange (SIOX) or DIOX profiles that are in general not well approximated by a triangular index profile, measurement accuracy can be reduced to the point of being unsatisfactory.

First Example DIOX Measurement

Figure 6:
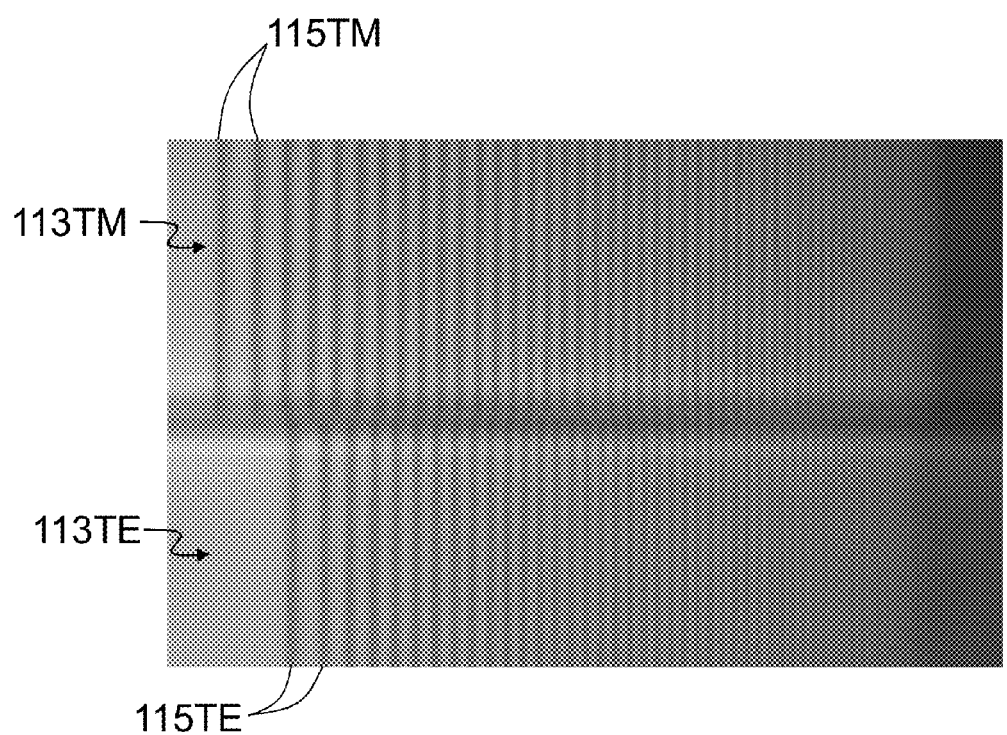
FIG. 6 is an example of a captured mode spectra for a single IOX substrate.

The above-described prism-coupling system 10 was used to make measurements on a waveguide 24 formed in substrate 20 by a DIOX process. Initially, a single IOX sample was produced with a first ion exchange step of 17.5 hours at 460° C. in a bath having about 57 wt-% NaNO$_3$, and 42.5% KNO$_3$, the balance being primarily silicic acid. The modified prism-coupling system 10 had a collection optical system 90 with a focal length f=200 mm, and photodetector 110 in the form of a CCD camera with 215 pixels/mm. The prism 40 was 25 mm×25 mm at coupling surface 44, and masks 45 were used on the input and output surfaces 42 and 46 define 7 mm wide slit apertures 47. This resulted in better visualization (imaging) of the closely-spaced mode lines 115. This measurement configuration may be used on the first step IOX of deep-DOL samples 20 that will later undergo a second step IOX for the formation of a shallow region R1. This sample was measured to obtain in the mode TM and TE mode spectra 113 TM and 113TE as shown in FIG. 6. The DOL for the example waveguide 24 for this first IOX step was determined to be in the range from 145 μm to 150 μm.

The sample was then subjected to a second IOX step of 15 min at 390° C. in a bath having at least 99 wt-% KNO$_3$ and approximately 0.5 wt-% NaNO$_3$, the balance being primarily silicic acid. This sample was then measured in prism-coupling system 10 to produce mode spectra 113TE and 113TM as shown in FIGS. 7A and 7B using two different configurations of the system, namely with light-blocking features 49 (FIG. 7A) and without the light-blocking features (FIG. 7B).

Figure 7A:
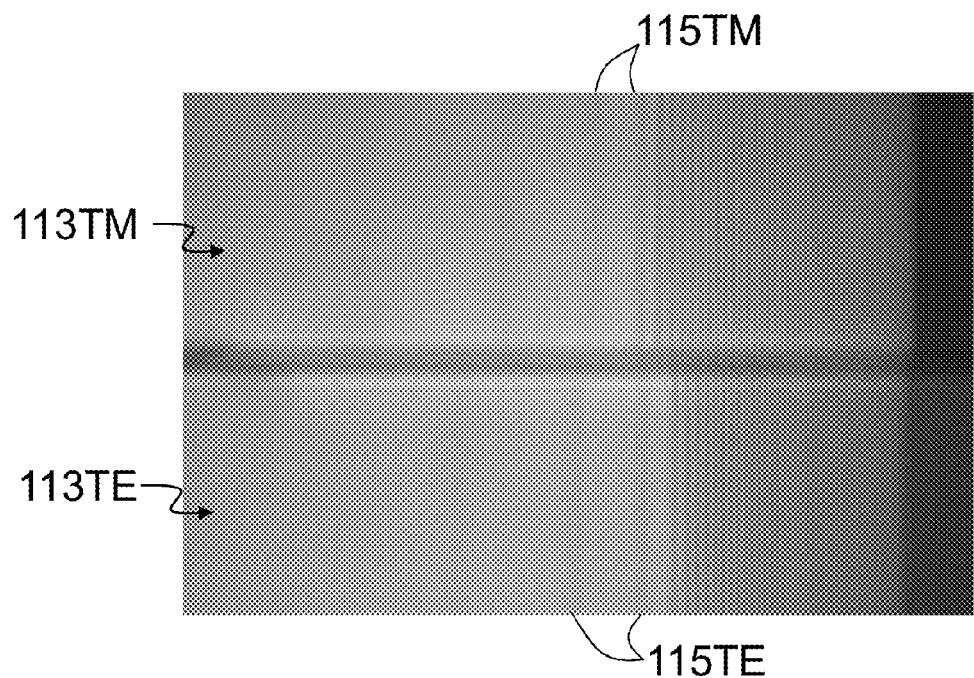
FIGS. 7A and 7B show the captured mode spectrum of the substrate of FIG. 6 after a second IOX process, wherein FIG. 7A includes the use of light-blocking features to improve contrast in the higher-order modes at the expense of the lower order modes, and wherein FIG. 7B does not use the light-blocking features so that the lower-order mode contrast is improved.
Figure 7B:
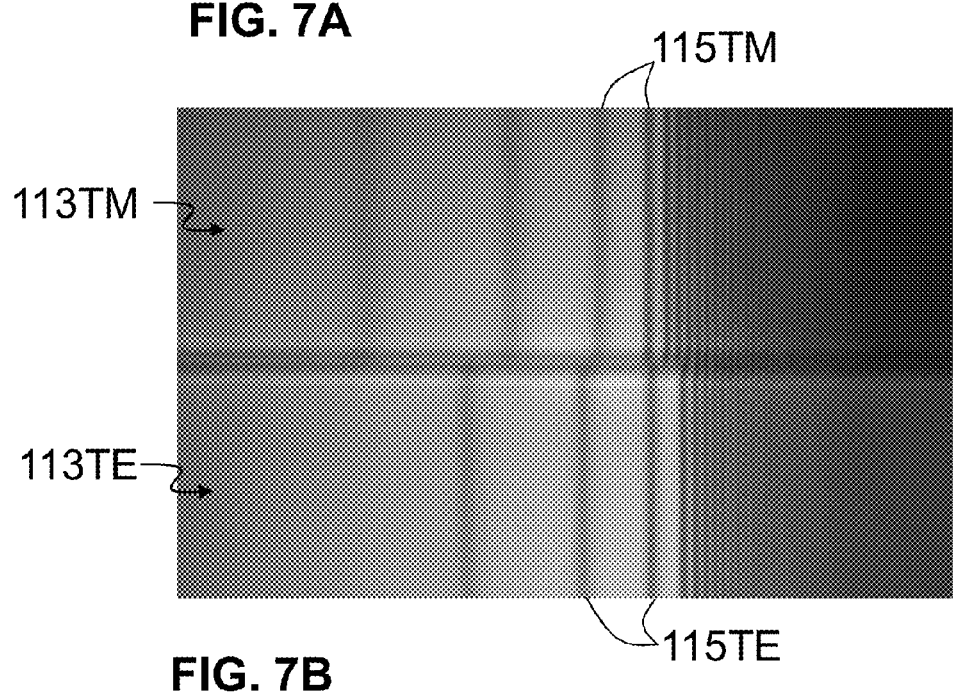

By comparing the mode spectra 113TM and 113TE of FIGS. 7A and 7B, the use of light-blocking features 49 makes the mode lines 115TM and 115TE for the second step IOX more visible (i.e., the contrast is increased) However, it also decreases the ability to measure the total number of mode lines 115 and therefore makes the determination of DOL more difficult. Also, due to the presence of the second IOX, the calculated DOL is erroneous due to the non-triangular (i.e., non-linear) shape of the index profile.

One could contemplate using the configuration of prism-coupling system 10 with the light-blocking members 49 to obtain the mode spectra of FIG. 7B to measure both first and second steps of the DIOX process, but this would be at the risk of an increased error in determining DOL in the first step of the IOX, and, in particular, under-estimating the DOL. This approach may work well enough for a DOL less than about 150 μm. However, for a DOL>150 μm, using the same system configuration for measurements of the first and second steps is accompanied by significant DOL error. Using the two different configurations for prism-coupling system 10 generally provides a better overall DOL measurement.

Second Example DIOX Measurement

In the following, embodiments utilizing two different configurations for system 10 for measurements after fabrication step 1 and step 2 are demonstrated using a prism-coupling system 10 having a similar prism 40 (25 mm×25 mm) and collection optical system 90 with a focal length f=200 mm, and photodetector 110 with slightly smaller pixels (227 pixels/mm, instead of 215 pixels/mm). An iris 93 with a maximum aperture of 12 mm was employed in photodetector system 130, as shown in FIG. 3A.

Figure 8:
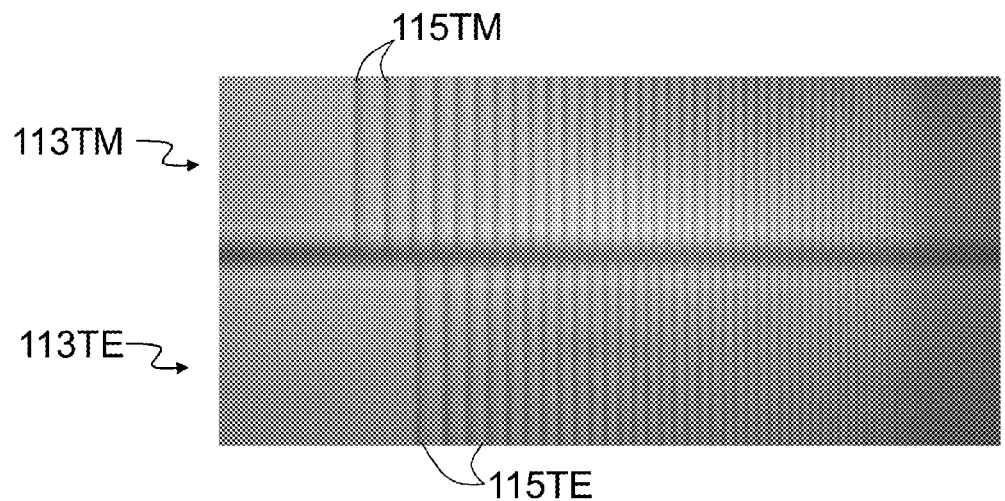
FIG. 8-14 are additional examples of mode spectra measured for various IOX substrates using different configurations of the prism-coupling system as described below.

FIG. 8 shows the fully resolved mode spectra 113TM and 113TE of the step 1 sample 20 produced as described above. Light-blocking features 49 were not used in the measurement, and the illumination was adjusted to allow the maximum illuminated length along the prism, for maximum resolution, with iris 93 wide open.

Figure 9:
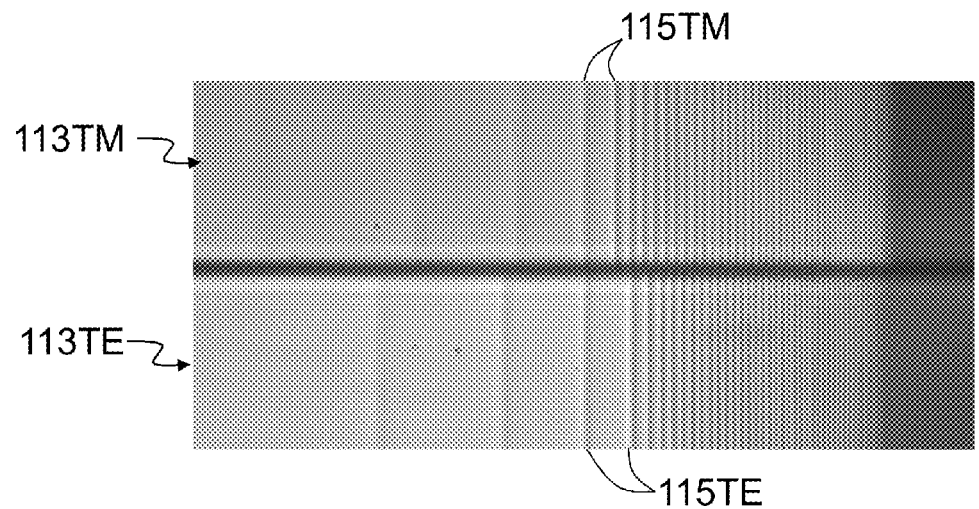

FIG. 9 shows the entire mode spectra 113TM and 113TE of the sample after the second IOX, taken with the same measurement conditions as used for measuring the spectra 113TM and 113TE of FIG. 8. The sparse mode lines 115TM and 115TE that correspond to the shallow region R1 have relatively low contrast.

Figure 10:
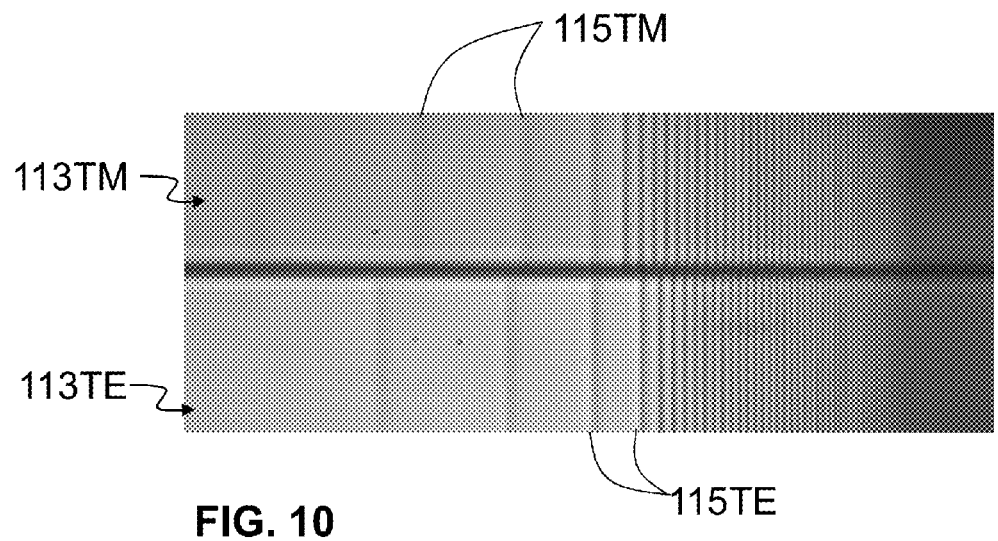

FIG. 10 shows the same mode spectrum as in FIG. 9, but after insertion of a light-blocking feature 49 that intruded into the top side of light beam 62S. The contrast of the sparse mode lines 115 is substantially improved, but the denser mode lines on the right side of the TM (top-half) spectrum are lost, compared to the spectrum of FIG. 9.

Figure 11:
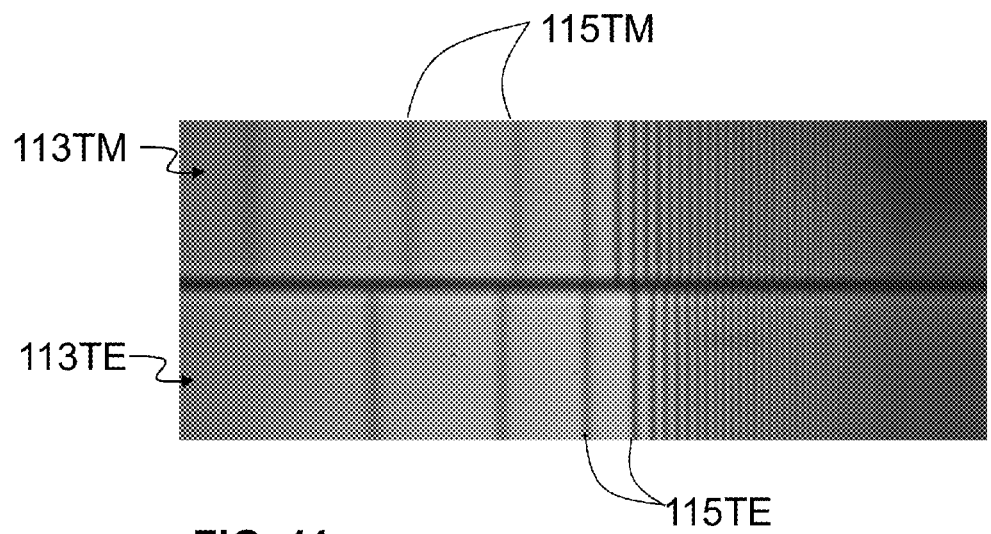

FIG. 11 shows the same mode spectra 113TM and 113TE as in FIG. 10 but taken without the light-blocking feature 49 and with the iris 93 having a reduced diameter of about 7 mm. The sparse mode lines 115 have high contrast, but one more mode line is unresolved in the dense mode line spectrum in the top half (TM). FIGS. 8 through 11 demonstrate an embodiment where a high contrast of the sparse mode lines 115 may be obtained using either iris 93 or a light-blocking feature 49 in the top side of the beam (see FIG. 3A).

Measurement of a DIOX mode spectra 113TM and 113TE having both a dense-mode line region and a sparse-mode line region provides limited ability to control the spike depth and the frangibility state of substrate 20. In particular, for some conventional prism-coupling systems, the results for CS, DOL, and CT are based on calculations that assume a single-segment linear truncated index profile, which is not a very accurate assumption for DIOX waveguides 24. From these three parameters, the depth of the spike is not determined, and the combination of CS, DOL, and CT after the step 2 IOX provides only partial means of control of frangibility. For example, if CS is below a certain upper limit, and DOL is in a certain range, then if CT is below a certain upper limit (for the particular thickness of interest), then the probability that the glass substrate is frangible is relatively low.

The frangibility limit in terms of CT is quite sharply determined for a one-segment linear profile, unlike the DIOX profile, particularly when the DOL is a small fraction of the substrate thickness. When the DOL is a substantial fraction of the substrate thickness (such as greater than 10%), then a one-segment profile can still have a well-defined frangibility limit, valid for a reasonably restricted range of DOLs in the neighborhood of the DOL of interest.

In an example, the DIOX profile can be effectively measured and controlled by using the assumptions based on a 1-segment-linear profile, if the following steps are taken:

1) For a particular range of DOLs of interest, a certain physical CT is found to associate well with a frangibility limit for a particular thickness.

2) Choose a final physical CT, not exceeding the physical CT frangibility limit, as the target physical CT after step 2.

3) Assign a preferred CT budget—a physical CT limit for step 1, and the rest to step 2. In an example, for a thickness ranging from 0.4 to 1 mm, the preferred range for the step 1 physical CT may include 0.8-0.89 of the total final physical CT. In an example, the physical CT for a monotonic stress profile can be found by finding the stress induced birefringence using the inverse-WKB method to recover the TE and TM index profiles on measured mode spectra of samples of interest, and applying force balance such that the integral of stress in the interior tension region equals the integral of stress in the compression region.

4) Assign an FSM-type CT limit for step 1, corresponding to the physical CT budgeted for step 1;

5) For fabrication control, measure FSM-type CS/DOL/CT after step 1, and ensure that FSM CT is below the FSM-CT limit for step 1.

6) Using empirical data, or modeling, assign an FSM-type CT limit for the spike based on the CS and depth of the spike. The depth of the spike is found by either a manual measurement where only the sparse modes are counted, or by automatic measurement as shown below, by a system arranged to resolve only the sparse modes of the spike.

The correspondence between the FSM-type CT limit for the spike, and the budgeted physical CT for the spike, may account for the typical CS of step 1. For example, if the step 1 CS is typically about 200 MPa, and the spike CS is about 800 MPa and the spike DOL is about 12 micrometers, then the FSM-type CT will be calculated for a thickness of 800 micrometers as follows:

$$CT_2^{FSM} = \frac{850 * 12}{800 - 2 * 12} = 13.14$$

On the other hand, the CS increase relative to the first step is about 850-200 MPa, so and FSM-type CT for the spike that may correlate better with the increase of physical CT with increase of the spike depth or CS is:

$$CT_2^{FSM} = \frac{(850 - 200) * 12}{800 - 2 * 12} = 10.05$$

In the selection of value of FSM-type CT to be observed by the spike measurement, the FSM-type CT increment corresponding to the physical CT budget for the spike, may be multiplied by a factor:

$$F_{CT}^{corr} = \frac{CS_2^{typical}}{CS_2^{typical} - CS_1^{typical}}$$

where the subscripts 1 and 2 indicate values after ion exchange step 1 and ion exchange step 2. The so-applied higher FSM-type CT limit accounts for neglecting in the measurement after step 2 the presence of substantial CS from step 1, and hence the CS change contributing to the CT increase from step 1 to step 2 is CS2−CS1, rather than CS2 only.

After the second IOX, substrate 20 is measured on prism-coupling system 10 as configured to measure the sparse modes of the spike of region R1. If some or most of the densely packed mode lines 115 of the deep region R2 are resolved automatically (e.g., by software), then a manual measurement mode can be used to capture and count only the sparse modes 116 confined in the spike region R1.

Alternatively, as described below, using a prism-coupling system 10 configured to resolve only the sparse modes 115 of the spike in region R1 allows for quick automatic measurement, for determining CS and DOL of the spike, as well as for determining an FSM-type CT limit of the spike. In a related embodiment, the spike may be required to have CS and DOL falling within prescribed ranges, selected to guarantee that the increase of physical CT due to the spike does not exceed the physical CT allowance for the spike, based on empirical data.

Figure 12:
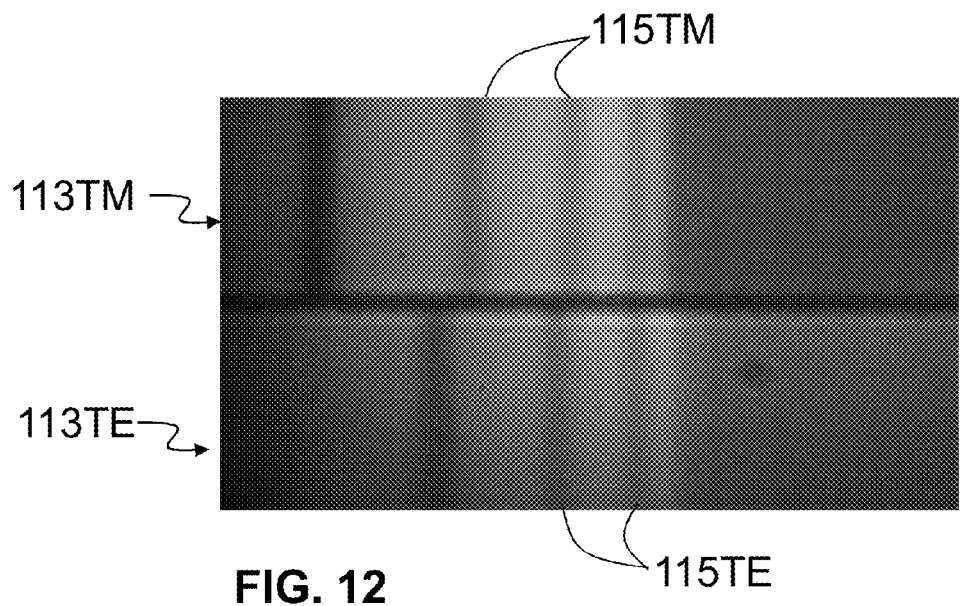

FIG. 12 shows example mode spectra 113TM and 113TE obtained using the prism-coupling system 10 configured as described above to capture the mode spectra of FIG. 11, but with a light-blocking feature 49 inserted adjacent the output face 46 of prism 40 to block a bottom portion of light 63R (see FIG. 3A) to substantially reduce the system resolution, especially for the high-order modes. The light-blocking feature 49 was positioned about 20 mm away from the bottom edge of the prism output surface 46, and about 5 mm in front of the iris 93, which was set to have a reduced diameter of about 5 mm. The light-blocking feature 49 was configured to upwardly extend to reaching slightly (about 1.5 mm) above the optical axis A2.

In FIG. 12, the sparse mode lines 115TM and 155TE are clearly resolved, and the space between the last of the sparse mode lines and the region of merged dense modes lines is visible and measurable. The prism-coupling system 10 can use the space between the last detected mode line 115 and the transition to the dark region to determine a fractional part of the total mode count, for a more precise estimate of the DOL. With the light-blocking feature 49 of this embodiment, prism-coupling system 10 can measure the DOL of the spike using to linear-profile assumption, and the CS and FSM-type CT can also be provided by the same measurement.

Figure 13:
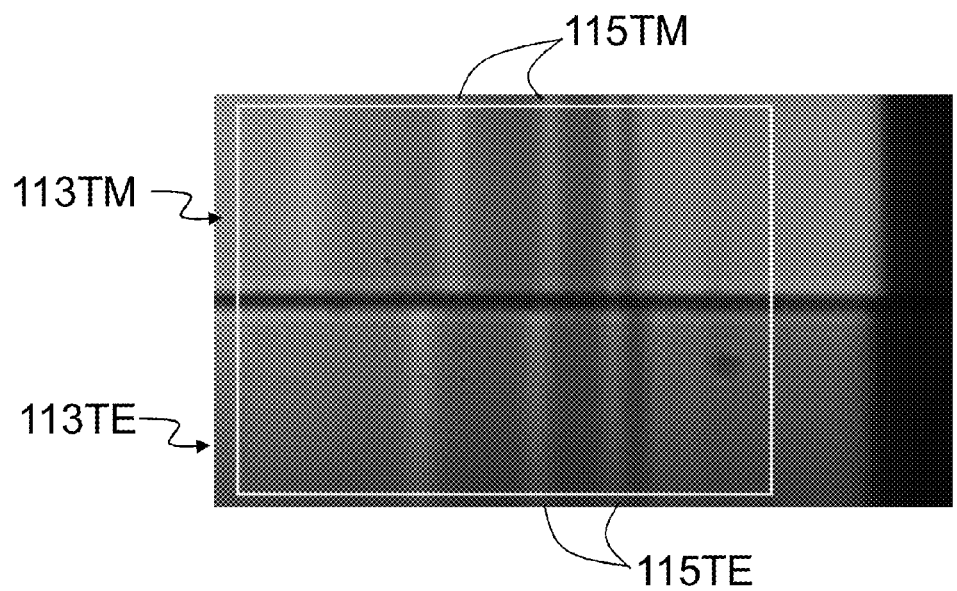

FIG. 13 shows example mode spectra 113TM and 113TE collected using the prism-coupling system 10 used to capture the mode spectra of FIG. 12, with the height of the light source 106 adjusted higher, resulting in light coupled back to the prism dominating the collected mode spectra. In an example, prism-coupling system 10 is configured to measure the mode lines 115 as bright lines. With properly chosen measurement area as shown by the white frame in FIG. 13, the measurement of the bright-line spectra proceeds in a way equivalent to the measurement of the dark spectrum, again allowing a quick, automated estimate of CS, DOL, and CT for the spike.

The above sequence describes an effective and fast method to ensure proper product fabrication by making measurements after each fabrication step using prism-coupling system 10 configured to optimally capture the important features of the spectrum for the different IOX steps.

In addition, a receiver of a final product may want to determine whether the DIOX substrate 20 as a product conforms to certain quality requirements. In this case, the measurement after step 1 is not available and the following method can be used:

1) Collect a mode spectra measurement using prism-coupling system 10 configured to collect the spike spectrum, as demonstrated in FIGS. 12 and 13. Ensure that the spike CS, DOL, and CT conform to the product requirements.

2) Collect partial dense mode spectra 113TM and 113TE, suppressing the mode lines 115 of the spike, and estimate a partial DOL of the deep region R2, and approximate CS under the spike. The limits on CS, DOL, and CT for this partial measurement may be set from empirical data for profiles that conform to all requirements, as measured after each fabrication step, or confirmed by a full stress profile analysis, such as using the IWKB method. Conformance of the measurement to these limits guarantees that the profile conforms to the specification, if the spike has already been confirmed to conform to its own specifications.

Figure 14:
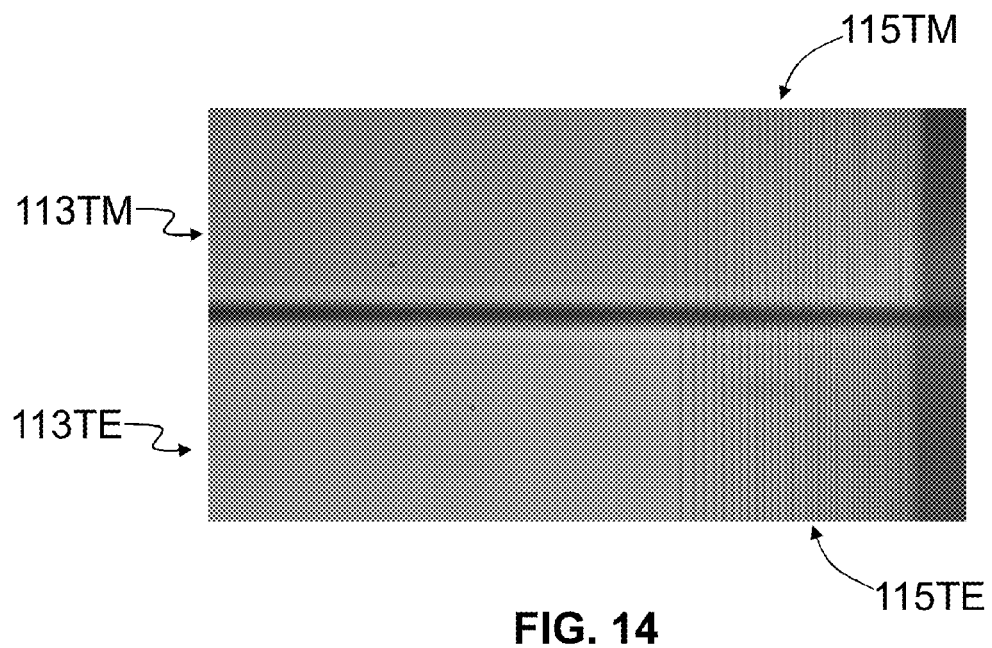

FIG. 14 shows TM and TE mode spectra 113TM and 113TE as collected for the same DIOX sample 20, but without light-blocking features 49 and without the iris 93 so that the full 23 mm aperture of the collection optical system 90 was employed. The height of light source 60 was adjusted to obtain high resolution for the densely spaced mode lines 115, and at the same time for low contrast for the low-order, sparse mode lines. In this regime, the processing software of prism-coupling system 10 can miss the sparse mode lines 115, and detect CS, and partial DOL for the deep region R2 underneath the spike.

To ensure the CS value underneath the spike is approximately correct, all spike mode lines are excluded from the processing of the TM and TE mode spectra 113TM and 113TE, while none of the highest-index mode lines 115 of the deep region R2 are missed. In the bottom region of FIG. 12, the leftmost of the easily resolved mode lines is actually the last of the region R1 mode lines. Hence, a more accurate estimate of the compression underneath the spike in region R1 may be obtained by eliminating this mode from the processing, e.g., by using the manual measurement mode.

Switchable Light-Blocking Feature

In another aspect of the disclosure, the light-blocking feature 49 used to eliminate the mode lines corresponding to the modes of the deep region R2 is switchable, i.e., can be selectively inserted into and out of the optical path OP1 or OP2 (see FIG. 3A). In an example illustrated in FIG. 5, the switchable light-blocking feature 49 is attached to an insertion/removal device 51 that is used to insert and remove the light-blocking feature from the optical path OP1 or OP2. In an example, the insertion/removal device 51 provides least one of a rotation and a translation motion. In this way, the measurement of the steep shallow region R1 can be obtained with the light-blocking feature 49 in place, immediately followed by a measurement of the dense spectrum of the deep region R2 after switching the light-blocking feature off (i.e., removing it from the optical path OP1 or OP2) and adjusting the measurement area to account the densely spaced mode lines only. In this way, two consecutive measurements can be performed on the same substrate 20. This makes for faster measurements and streamlines the quality-control process.

In an example, a mechanical stop (not shown) may be used to ensure that the light-blocking feature 49 is inserted to the same height h in each measurement of the shallow region R1 of the profile. In addition, two light-blocking features 49 on either side of the prism 40 may be used, and controlled independently by two insertion/removal devices 51, or simultaneously by a single insertion/removal device. In an example, insertion/removal device can be in the form of a lever or other simple mechanical or electro-mechanical implement.

IR-Based Systems and Methods for Super-DOL Measurements

For DIOX waveguides with DOL values that are greater than 70 μm or 100 μm or even 150 μm, further modifications to the above-described prism-coupling systems and methods can be implemented that result in greater measurement accuracy, e.g., with standard deviations for the DOL below about 2 μm, or about 1%.

In an example, the light source 60 of prism-coupling system 10 is or includes a near IR light source having a wavelength of between $\lambda=700$ nm to 2200 nm. However, due to the wide use of silicon cameras in CCD format or CMOS format, wavelengths between $\lambda=700$ nm to 1100 nm are particularly convenient. For wavelengths between $\lambda=1100$ nm to 2200 nm, non-Si detectors such as InGaAs, InP, Ge, HgCdTe or alternative bolometric/heat sensors or upconverters via phosphorescence from near-IR to visible in that range can be used. Another range of interest is in the mid-IR from 3.5 um to 5.5 um, which requires cameras using InAs technology or HgCdTe technology.

With reference again to FIG. 2 and the example refractive index profile for a DIOX waveguide shown therein, a first IOX is used to generate the deep diffusion to define region R2. In region R2, optical modes are very dense as the diffusion gets deeper into the glass substrate. A second IOX can then be used to modify the refractive index and the stress profile. This second IOX leads to an upper, shallow region R1 that has spike in the index profile near the surface 22 and has optical modes that are relatively well spaced. For this particular case of a "spike+tail profile" using a double IOX, the mode lines 115 form a sparse region followed by a more dense region.

The number of mode lines 115 present in the mode spectrum 113 of a near-IR imaging prism-coupling system 10 is smaller than for a visible-wavelength prism-coupling system that operates at a wavelength of λ=589 nm. This reduction in the number of modes leads to a better visualization and quantification of the number of mode lines 115 and the mode-line spacing relative to the pixel size of photodetector 110. This in turn allows for a more accurate measurement of the DOL with a lower standard deviation for large DOL values. This is particular true for the dense region of the modes on the tail of region R2.

With reference again to FIG. 3A, an example prism-coupler 10 is configured to measure deep DOL samples in a deep SIOX and double IOX scenario. The example configuration includes the larger prism 40, e.g., 25 mm×25 mm, and includes mask 45 with a slit opening 47 having a width in the range between 1 mm and 20 mm. The use of mask 45 and slit opening 47 is optional on output surface 46 of prism 40. The example configuration also includes light-blocking features 49 adjacent to the prism 40 at both in the input and output sides 42 and 46.

When detecting the fundamental or low-order modes in a spiked dual-IOX region, light-blocking features 49 reduce the mode coupling and angular distribution of the fundamental and lower order modes that are more separated at photodetector 110, making them more easily visible. However, as noted previously, they also decrease the contrast of the high-order modes that are numerous and more closely spaced. There is therefore a trade-off of visualization of lower-order modes and high-order modes in the case of a DIOX index profile, and the size of the light-blocking features is chosen accordingly.

The use of light-blocking features 49 is optional when measuring the CS/DOL of single IOX and for the DOL of double IOX or higher IOX processes. The light-blocking features 49 are employed when measuring the CS/DOL of the spike region R1 when this region has a very steep index profile.

Figure 15:
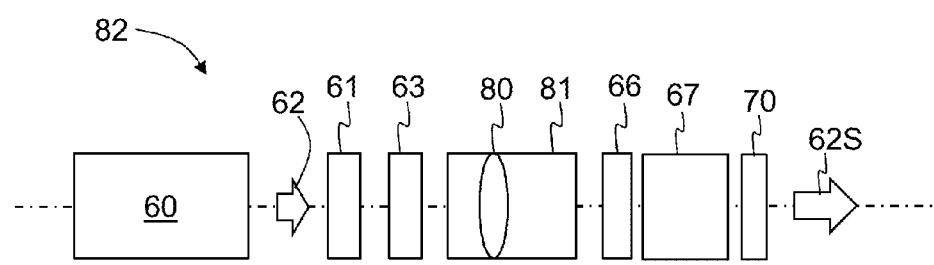
FIG. 15 is a schematic diagram of an example of an infrared (IR) light source for use in the prism-coupling system of FIG. 3A.

FIG. 15 is cross-sectional partially exploded view of an example IR-based light source system 82. An example light source 60 includes an LED that emits light 62 at having a wavelength λ=850 nm and with 900 mW of optical power. The focusing optical system 80 is supported by a lens tube 81, with the focusing optical system having a relatively short focal length, e.g., f=16 mm. The light source 60 is operably connected to lens tube 81 via a connector 61 and a tube holder 63. The filter 66 is a narrow band-pass filter, e.g., 4 nm, and the light-scattering element 70 has for example a grit of between 200 and 1500. The filter 66 and light-scattering element 70 are operably connected via a short length of tube spacer 67.

The short-focal-length lens 80 serves to capture most if not all the light 62 emitted from the LED light source 60 and redirects the light. The angular diffused light is filtered by the narrow band-pass filter 66. The dispersion of the glass used for prism 40 has the detrimental effect of broadening the mode lines 115 observed and weakening their contrast when broadband light is used. The use of filter 66 thus mitigates this adverse dispersion effect. The light 62 is then diffused by light-scattering element 70. The light-scattering element 70 is configured to be effective at providing the desired redistribution of the angular spectrum of the light 62 from light source 60 when combined with an appropriate focusing (condenser) optical system 80. Higher grit values for light-scattering elements that result in less scattering loss can be used when the amount of optical output power in light beam 62S is a concern.

The typical spectral response of a CCD camera that uses silicon-based sensors is limited to around 1100 nm, has a maximum response at about 500 nm, and has a response of about 20% of the maximum response at 850 nm. Thus, when using an operating wavelength of 850 nm for light source system 82, the CCD-based photodetector 100 is preferably operated at maximum gain.

The above-described modified IR-based prism-coupling system 10 was used to measure the mode spectra for a substrate after subjecting it to a single IOX process. The IOX sample 20 was produced with a first IOX of 14.0 hours at 460° C. in a bath having about 49 wt-% $NaNO_3$, and 51% $KNO_3$. The mode lines 115 were clearly visible and their separation was clearly seen. The DOL was determined to be about 144 μm for the sample.

The single-IOX substrate 20 was then subjected to a second IOX of 15 min at 390° C. in a bath having at least 99 wt-% $KNO_3$ and approximately 0.5 wt-% $NaNO_3$, the balance being primarily silicic acid. The mode spectrum of the DIOX substrate was then measured. The mode lines 115 were clearly visible and clearly separated. By ignoring the first two or three mode lines 115 and measuring only the remaining sharper and closely spaced mode lines, one can evaluate the DOL of the first IOX even after the presence of the spike generated by the second IOX. This is convenient from the manufacturing point of view as one may get critical parameters of the first IOX process after the second step IOX.

The DIOX sample 20 was then measured to produce mode spectra using two different configurations of prism-coupling system 10. Table 1 below sets forth the results for 16 consecutive measurements of the DIOX sample 20 as described above using the IR-based (850 nm) prism-coupling system 10. In Table 1, "#" is the measurement number, "<DOL>" is the average DOL, "$DOL_U$" is the upper DOL, and "$DOL_L$" is the lower DOL, with all DOL values measured in microns (μm).

TABLE 1

| # | Stress (MPa) | <DOL> | $DOL_U$ | $DOL_L$ |
|---|---|---|---|---|
| 1 | 229.325 | 144.476 | 144.288 | 144.664 |
| 2 | 231.364 | 145.094 | 145.103 | 145.085 |
| 3 | 232.619 | 144.09 | 143.82 | 144.361 |
| 4 | 233.791 | 144.438 | 144.449 | 144.536 |
| 5 | 230.173 | 144.902 | 144.731 | 145.072 |
| 6 | 2332.18 | 144.064 | 143.404 | 144.724 |
| 7 | 233.442 | 144.262 | 144.23 | 144.293 |
| 8 | 231.875 | 144.965 | 144.553 | 145.378 |
| 9 | 233.842 | 144.258 | 143.958 | 144.558 |
| 10 | 232.155 | 142.361 | 143.827 | 140.896 |
| 11 | 232.808 | 142.421 | 144.025 | 140.816 |
| 12 | 230.632 | 144.713 | 143.985 | 145.44 |
| 13 | 230.77 | 145.661 | 146.511 | 144.812 |
| 14 | 233.99 | 144.719 | 144.724 | 144.713 |
| 15 | 228.557 | 144.408 | 143.808 | 145.007 |
| 16 | 234.647 | 144.186 | 143.439 | 144.933 |
| Average | 232.03 | 144.31 | 144.40 | 144.33 |
| Stdev | 1.83 | 0.86 | 0.75 | 1.39 |

From Table 1, the average $DOL_U$ based on the TM modes was $DOL_U$=144.31 μm with a stdev of about 0.75 μm. The reduction in the standard deviation is remarkable from the previous standard deviation in the 3-4 μm range for measurements taken at a wavelength of λ=589 nm.

Additional light-blocking features 49 can be used to make the mode lines 155 of the second step IOX more visible. However, it decreases the ability to measure the total number of mode lines and therefore makes the determination of the DOL more difficult. Also due to the presence of the second IOX the DOL found by the instrument software is also erroneous due to the non-triangular shape of the index profile.

In order to measure the spike region R1 more accurately, including the CS of the spike and the depth of the spike region, the light-blocking features 49 are needed, but in this case one can use the original visible wavelength of λ=589 nm in the visible or alternatively a shorter wavelength around 2λ, =400 nm, which is in the other lower range of the absorption spectrum of the silicon based cameras.

In order to limit the dispersion broadening of the mode lines 115 in the mode spectrum, a band-pass filter 66 centered at 850 nm and having a transmission bandwidth of about 4 nm full-width at half-maximum (FWHM) is employed. For measurements at an IR wavelength λ where the DOL is greater than about 150λ, in an example the light source system bandwidth at FWHM should be less than about 0.007λ, and preferably below 0.005λ.

Measurement Systems and Methods Using Shape Control

In certain instances, decreased DOL measurement precision resulting from the deterioration of the contrast of the mode lines in the mode spectra can be due to the sample being warped or otherwise misshapen. In particular, small variations in warp between different samples cause significant difficulty when trying to measure these samples quickly in a prism-coupling system. More careful measurements, including very careful orientation of the sample to minimize the warp along the measurement direction, as well as use of longer wavelength, and limiting the dispersion broadening of the mode lines, have helped obtain better measurements in this very large DOL range. On the other hand, avoiding having to readjust a sample during measurements is a valuable in practice as it would substantially reduce measurement time. The problem has come to the fore because of recent emphasis on producing samples with large DOL that have improved damage resistance when used as a cover-glass of a portable device, such as a smartphone.

When the DOL formed by an IOX process is very large (for example, >100 microns), it confines a very large number of optical modes, and the mode lines 115 formed by coupling to these modes are very densely spaced in the angular spectrum, and at the detector plane 92 (see FIGS. 3A-3C). In this case, small optical aberrations in the measurement that compromise the resolution can prevent resolving the mode lines and measuring the DOL and the stress profile correctly. Once source of such detrimental optical aberration is warp in the substrates 20.

Figure 16:
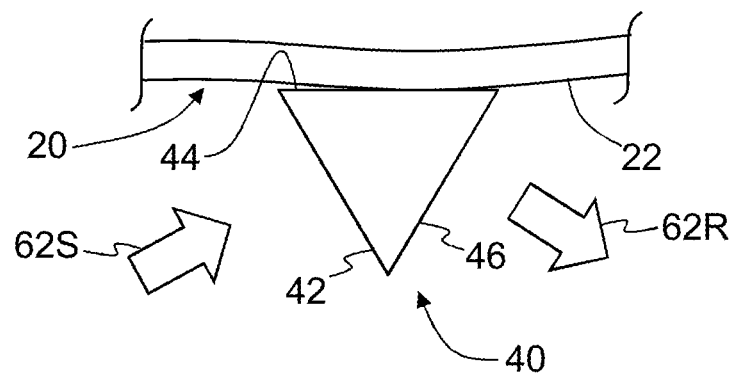
FIG. 16 is a close-up side view of a prism and an example warped substrate interfaced with the coupling surface of the prism.

FIG. 16 is a close-up view of prism 40 in contact with a substrate 20 that is warped so that the substrate surface 22 is non-flat. The warp in substrate 20 causes a parallel beam of light 62S from the input side 42 of the prism 40 to be transformed into a non-parallel beam 62R on the output side 46 of the prism. If the prism-coupling system 10 is not set up to account to this warp-induced divergence or convergence of the measurement light, then the mode lines 115 detected by photodetector 110 will be blurred due to the warp. The substrate warp thus constitutes a source of optical aberrations in prism-coupling system 10.

In principle, a small amount of warp that is repeatable from one sample to the next can be pre-compensated by biasing the distance between the collection optical system 90 and the photodetector 110 (see FIG. 3A) such that the sharpest mode lines 115 are obtained in the presence of this repeatable warp. This can work, for example, when warp is induced by gravity. If all samples have the same size and are made of the same material, the gravity-induced warp will be the same, and the collection optical system 90 can be biased to produce sharp mode lines 115 for the warped samples. On the other hand, it would then produce mode lines 115 with reduced sharpness for samples that do not have the same warp.

A more serious problem in making accurate measurements comes from warp that varies in magnitude and shape from sample to sample. For example, the warp may be spherical, parabolic, hyperbolic, saddle-shaped, cylindrical, conical, or some other shape. Typically it represents a deviation from the preferred flat shape. A deviation with a magnitude that is measured in the tens of microns or more and is not repeatable from one sample to the next is a major problem for proper waveguide characterization and prevents fast quality-control measurements.

Prism-Coupling System with Chuck Assembly

Figure 17:
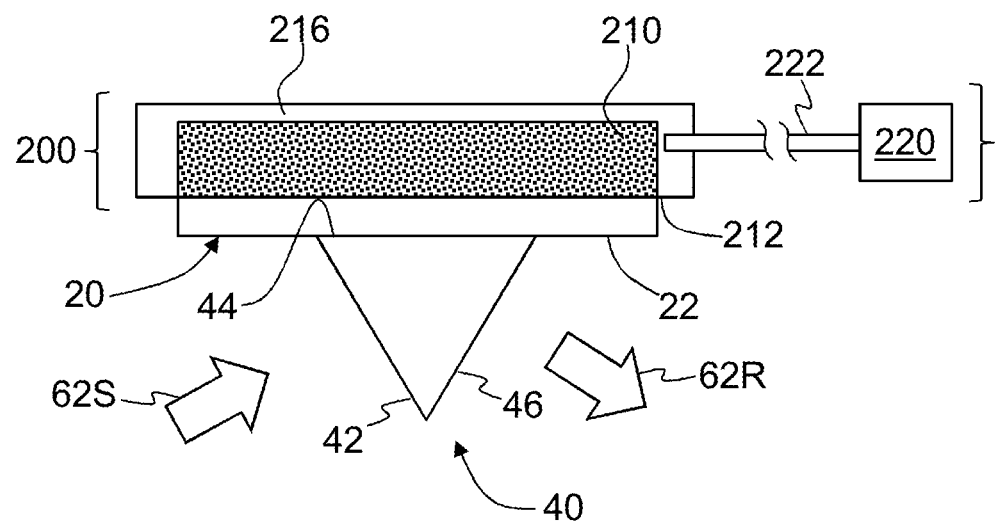
FIG. 17 is a close-up side view of a prism and a substrate, wherein the substrate is supported by an example chuck assembly that uses a vacuum to cause the substrate shape to substantially conform to the shape of a platen in the chuck assembly.

FIG. 17 is similar to FIG. 16 and illustrates an embodiment of a prism-coupling system that includes a chuck assembly 200. The chuck assembly 200 includes a platen 210 having an upper surface 212. The platen 210 is made of a stiff material of adequate thickness so that it does not bend. The platen 210 is pneumatically connected to a vacuum source (e.g., a vacuum pump) 220 via a vacuum line 222. The platen 210 is configured to convey a vacuum to the platen surface 222, wherein the vacuum forces the sample to substantially conform to the platen surface shape. The chuck assembly thus makes it possible for all samples 20 being measured to have substantially same shape during measurements.

In an example, platen 210 is made of stiff porous material such as porous aluminum, and is enclosed in a holder 216. The chuck transmits some of the vacuum from vacuum line 222 to the sample via the pores in the platen 210, and the ambient pressure forces the sample to comply to the shape of the platen surface 212. In another example, platen 210 includes a number of channels 218 (see, e.g., FIG. 18) that lead from vacuum line 222 to platen surface 212.

Example mode spectra were taken with and without the use of chuck assembly 200 to illustrate the improvement of the sharpness (contrast) of the mode spectrum when measuring a sample having DOL of about 100 microns. Even in this case of moderately large DOL, it was observed that the chuck assembly 200 provided improved mode spectra, i.e., one with higher contrast, while avoiding having to otherwise adjust the sample position.

In an example, platen 210 may have hardness exceeding the hardness of the glass substrate 20 being measured. In this case, in an example a thin porous coating of soft material such as Teflon or some other plastic may be disposed on the contacting surface of the platen 210, to prevent scratching of the glass substrate.

In an example, the platen 210 has cylindrical shape with a diameter ranging from about 20 mm to about 100 mm, and thickness ranging from about 5 mm to about 30 mm. The sample 20 is contacted by one of the flat or near-flat bases of the cylinder. To reduce the chance of scratching the glass surface, the circular edge of the holder 216 may be beveled at an angle between about 1 degree and about 45 degrees. In an example, the vacuum in the vacuum line 222 connected to the platen 210 may be in the range from about −0.1 bar to about −1 bar.

In one approach of the method, the sample 20 is brought in proximity to the platen surface 212 until the suction from the platen causes the sample to attach to the platen. The platen 210 is moved toward the coupling surface 44 of the prism 40 on which is disposed a droplet of refractive-index liquid, such that the sample is contacted to the prism optically through the refractive-index liquid. The refractive index liquid may have index approximately equal to the prism index. In another embodiment, the refractive-index liquid may have index lower than that of the substrate to be measured.

In another approach of the method, refractive-index liquid is applied on the coupling surface 44 of the prism 40, then the sample is disposed on top of the refractive-index liquid, and the platen 210 is brought in contact with the sample, applying suction to impart the desired always-identical shape on the sample.

The embodiment of prism-coupling system 10 that employs chuck assembly 200 is able to produce high-resolution, sharp spectra for a pre-defined shape, and ensure that all substrates that are brought for measurement generally conform to the platen surface shape to within sub-wavelength precision during the measurements. In one example, the platen surface 212 is made as flat as possible for measurements of nominally flat substrates. In practice, a platen 210 wherein surface 212 is slightly convex with about a 2-micron dome-height, provides a benefit for measurement of a large number of samples having a DOL ranging from about 110 to about 160 microns, as long as the collection optical system 90 is properly focused.

The above-described chuck-based embodiments of prism-coupling system 10 work well when the sample thickness is very uniform. If the sample thickness varies significantly over the measurement area, and this variation is different from one sample to the next, then adopting the shape of the chuck on the back surface of the sample may not guarantee that the coupling surface 22 will have the same shape every time.

Figure 18:
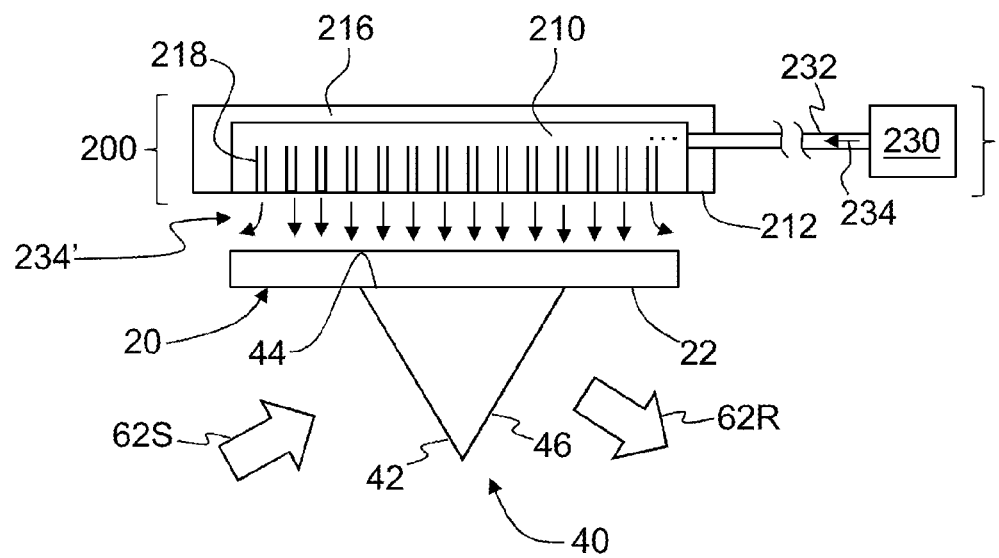
FIGS. 18 and 19 are similar to FIG. 17 and illustrate an example of a chuck system that provides an air cushion that causes the substrate to substantially conform to the shape of the coupling surface of the prism, with FIG. 19 showing a sealing ring between the platen and the back of the substrate to help confine the air cushion.

FIG. 18 is similar to FIG. 17 and illustrates an example configuration of prism-coupling system 10 wherein the chuck assembly 200 provides a gas cushion 234' by creating a region of high pressure adjacent platen surface 212. In this configuration, vacuum source 220 is replaced by a gas source 230, and vacuum line 222 becomes gas line 232 to carry a gas 234, which can be air or an inert gas such as nitrogen. Platen 210 is shown with channels 218 that carry gas 234 to the platen surface 212 to form the gas cushion 234'. The gas cushion 234' serves to press the sample uniformly against the prism coupling surface 44. This tends to force the sample coupling surface 22 to substantially conform to the shape of the prism coupling surface 44. This embodiment works for samples with moderate thickness variation across the measurement area. This is because it is the coupling surface 22 that interfaces with the prism coupling surface 44 that needs to conform to the shape of the prism coupling surface. Note that the space between the platen surface 212 and the sample 20 is greatly exaggerated in FIG. 18, and in practice the separation can be measured in microns.

Figure 19:
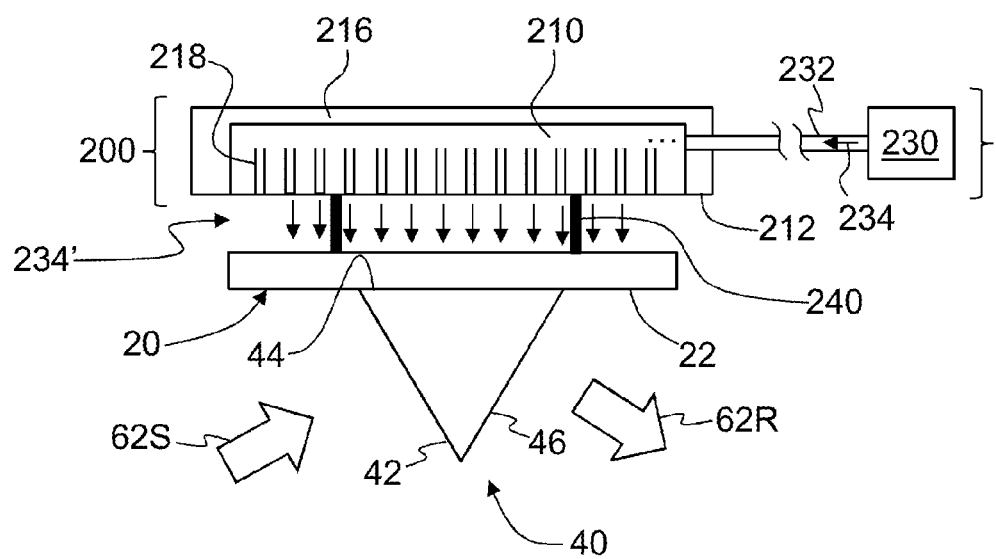

In one example, the flow gas 234 through platen 210 is impeded only by the glass substrate that resides adjacent platen surface 212. FIG. 19 is similar to FIG. 18 and illustrates an example embodiment that additionally includes a sealing ring 240 on platen surface 212. The sealing ring 240 substantially prevents the pressurized gas 234 from escaping from the space between the platen surface 212 and the substrate, thereby creating a more effective application of pressure via gas cushion 234'. Said differently, the sealing ring 240 helps contain the gas cushion 234'. The sealed area is preferably no larger than the area of the prism coupling surface 44, but may be somewhat larger than the measurement area. The measurement area on the prism coupling surface 44 may be smaller than the entire area of the coupling surface, which is achieved by use of the aforementioned light-blocking features 49.

Prism with Channels

FIGS. 29A and 29B are elevated views of an example prism 40 that includes channels 48 that run from the top flat surface 41 to the bottom coupling surface 44. The channels 48 can branch out so that there are more channel openings at the bottom coupling surface 44 than at the top surface 41, as illustrated in FIG. 29B. Channels 48 are pneumatically coupled at the top flat surface 41 to a vacuum source 220 (not shown; see FIG. 17). This creates a vacuum at bottom coupling surface 44 via channels 48.

The uniform surrounding atmospheric pressure forces the sample 20 be pressed against coupling surface 44 and adopt its shape. At least one channel 48 can be used, but as shown in FIG. 28, a row of several (two or more) channels may be used for more uniform application of vacuum across the measurement area.

The channels 48 are arranged so that light 62S and 62R is not incident upon the channels during a measurement. In an example, the spacing of inner surfaces of the two rows of channels 48 is preferably greater than about 5 mm, and in an example is much better greater than about 8 mm. In an example, the diameters of the channels 48 starting from the prism top 41 can be between about 0.5 an 1.5 mm. The spacing of channels 48 at the prism coupling surface 44 along each row should be preferably smaller than about 1 cm center-to-center. The channel openings in the two rows may be staggered to improve the uniformity of vacuum application across the measurement area.

In a related example, the channels 48 can be drilled in a metal prism holder, whose upper surface is co-planar with the prism coupling surface. The metal may be aluminum, copper, brass, or stainless steel. In another embodiment, the metal may be porous aluminum as described in the chuck design, again with its surface c-planar with the prism coupling surface. This co-planar requirement may be satisfied by gluing the prism to the metal holders on a flat alignment surface, or even by polishing the prism with the metal holder glued to it.

In a related embodiment, the prism 40 with suction capability may be flipped upside down, such that the measured sample is underneath the prism. The sample may hang from the prism, held thereto by the applied suction from the prism or prism assembly.

Finally, in another embodiment, the application of a vacuum to the substrate by the prism or prism and the prism holder may be combined with the application of pressure by a chuck assembly on the other side of the sample, for a combined effect of forcing the measurement surface to adopt the shape of the coupling surface of the prism. This embodiment can have two configurations: One with the prism underneath the sample, and one with the prism above the sample, and the chuck assembly 200 underneath the sample.

It will be apparent to those skilled in the art that various modifications to the preferred embodiments of the disclosure as described herein can be made without departing from the spirit or scope of the disclosure as defined in the appended claims. Thus, the disclosure covers the modifications and variations provided they come within the scope of the appended claims and the equivalents thereto.

What is claimed is:

1. A method of characterizing a double ion-exchanged (DIOX) waveguide formed in a substrate, comprising:

performing a first ion-exchange in the glass substrate to form the waveguide, the waveguide having a deep ion-exchange region with a first profile and a depth-of-layer (DOL);
capturing a first mode spectrum of the waveguide and determining the DOL from the first mode spectrum;
performing a second ion-exchange in the glass substrate to alter the first profile and to define a shallow ion-exchange region with a steep profile;
capturing a second mode spectrum of the waveguide by partially blocking a portion of the mode spectrum associated with the deep ion-exchange region to improve the contrast of a portion of the mode spectrum associated with the shallow ion-exchange region; and
determining from the improved-contrast second mode spectrum at least one of a compressive stress, a tensile strength, and a surface stress of the waveguide for the shallow ion-exchange region.

2. The method according to claim 1, wherein capturing the first mode spectrum includes performing a prism-coupling measurement with near-IR light and wherein capturing the second mode spectrum includes performing a prism-coupling measurement with visible light.

3. The method according to claim 1, wherein the first and second mode spectra are captured using a prism-coupling system and wherein partially blocking of a portion of the mode spectrum includes operably arranged at least one light-blocking feature adjacent a coupling prism of the prism-coupling system.

4. The method according to claim 1, including operably supporting the substrate on a chuck assembly to define a shape of the substrate when capturing the first mode spectrum and the second mode spectrum.

5. A method of characterizing a double ion-exchanged (DIOX) waveguide formed in a substrate, comprising:
performing a first ion-exchange in the glass substrate to define deep ion-exchange region with a shallow profile and a depth-of-layer (DOL) greater than 100 µm;
capturing with a prism-coupling system operating at an IR wavelength a first mode spectrum of the waveguide and determining the DOL from the first mode spectrum;
performing a second ion-exchange in the glass substrate to define a shallow ion-exchange region with a steep profile;
capturing a second mode spectrum of the waveguide by partially blocking a portion of the mode spectrum associated with the deep ion-exchange region to improve the contrast of a portion of the mode spectrum associated with the shallow ion-exchange region while reducing the contrast of the portion of the mode spectrum associated with the deep ion-exchange region; and
determining from a low-order-mode portion of the improved-contrast second mode spectrum at least one of a compressive stress, a tensile strength and a surface stress of the waveguide for the shallow ion-exchange region.

6. The method according to claim 5, including capturing the second mode spectrum using visible light.

7. The method according to claim 6, wherein the prism-coupling system includes a prism, and wherein the first and second mode spectra are captured without moving the glass substrate relative to the coupling prism.

8. The method according to claim 5, wherein the prism-coupling system includes a prism with input and output sides, and wherein partially blocking a portion of the mode spectrum is performed by arranging at least one light-blocking feature relative to at least one of the input and output sides of the prism.

9. The method according to claim 5, wherein the IR wavelength is nominally 850 nm.

10. A measurement system for measuring at least one characteristic of a double ion-exchange (DIOX) waveguide formed in a substrate to include a deep region and a shallow region, wherein the waveguide includes lower-order and higher-order modes that define a mode spectrum, the system comprising:
a coupling prism having an input surface, an output surface and a coupling surface, and wherein the coupling surface interfaces with the waveguide at a substrate upper surface, thereby defining a substrate-prism interface;
a light source system that emits light that illuminates the substrate-prism interface through the input surface of the prism, thereby forming reflected light that includes mode lines of the mode spectrum, wherein the reflected light exits the output surface of the coupling prism;
at least one light-blocking feature arranged relative to the coupling prism and configured to limit the amount of light from the light source that couples into higher-order modes of the waveguide;
a photodetector system having a detector and arranged to receive the reflected light from the coupling prism and detect a mode spectrum on the detector, wherein the mode spectrum has a higher resolution for the lower-order modes as compared to if the at least one light-blocking feature was absent; and
a controller configured to process the detected a mode spectrum to determine the at least one characteristic of the waveguide, wherein the at least one characteristic includes a surface stress, a compressive stress and a tensile strength of the shallow region.

11. The measurement system according to claim 10, further including at least one mask arranged on at least one of the prism input and output surfaces, wherein the at least one mask defines a slit aperture having a width in the range from 0.2 mm to 20 mm.

12. The measurement system according to claim 10, wherein the light source system includes an infrared (IR) light source.

13. The measurement system according to claim 10, wherein the light-blocking features are configured to be inserted into and removed from an optical path between the light source system and the photodetector system.

14. A measurement system for measuring at least one characteristic of a double ion-exchange (DIOX) waveguide formed in a substrate to include a deep region and a shallow region, wherein the waveguide includes lower-order and higher-order modes that define a mode spectrum, the system comprising:
a coupling prism having an input surface, an output surface and a coupling surface, and wherein the coupling surface interfaces with the waveguide at a substrate upper surface, thereby defining a substrate-prism interface;
a chuck assembly that operably supports the substrate and defines a shape for the substrate;
a light source system that emits light that illuminates the substrate-prism interface through the input surface of the prism, thereby forming reflected light that includes mode lines of the mode spectrum, wherein the reflected light exits the output surface of the coupling prism;

a photodetector system having a detector and arranged to receive the reflected light from the coupling prism and detect the a mode spectrum on the detector; and a controller configured to process the detected a mode spectrum to determine the at least one characteristic of the waveguide, wherein the at least one characteristic includes a surface stress, a compressive stress and a tensile strength.

15. The system according to claim 14, further including at least one light-blocking feature arranged relative to the coupling prism and configured to limit the amount of light from the light source that couples into higher-order modes of the waveguide.

16. The system according to claim 14, wherein the light from the light source is diffuse and has an IR wavelength.

17. The system according to claim 14, wherein the light source includes a light-emitting diode and a diffuser, and wherein the light has a wavelength of 850 nm, and wherein the light source system includes an optical filter having a bandwidth of about 4 nm.

18. The system according to claim 14, wherein the chuck assembly includes a platen with an upper surface and that is configured to deliver a vacuum to the platen upper surface, and wherein the vacuum serves to hold the substrate to the platen surface in a manner that causes the substrate upper surface to substantially conform to the platen surface.

19. The system according to claim 14, wherein the chuck assembly includes a platen with an upper surface and that is configured to deliver a gas to the platen upper surface to form a gas cushion that pushes the substrate against the coupling surface of the prism in a manner that causes the substrate upper surface to substantially conform to the coupling surface.

20. A method of performing prism coupling of a substrate having a waveguide having an upper surface and a coupling surface of a prism, comprising:

providing a vacuum via through channels that are open at the coupling surface; and bring the waveguide upper surface into contact with the prism coupling surface such that the vacuum causes the waveguide upper surface to be pressed against and substantially conform to the coupling surface of the prism.

* * * * *